(12) United States Patent
Wendt et al.

(10) Patent No.: US 11,952,609 B2
(45) Date of Patent: Apr. 9, 2024

(54) METHODS OF PRODUCING SUCCINIC ACID FROM A BIOMASS

(71) Applicant: Battelle Energy Alliance, LLC, Idaho Falls, ID (US)

(72) Inventors: Lynn M. Wendt, Idaho Falls, ID (US); Bradley D. Wahlen, Rigby, ID (US); Birendra Adhikari, Ammon, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 17/652,835

(22) Filed: Feb. 28, 2022

(65) Prior Publication Data

US 2022/0275408 A1    Sep. 1, 2022

Related U.S. Application Data

(60) Provisional application No. 63/200,311, filed on Mar. 1, 2021.

(51) Int. Cl.
 C12P 7/46     (2006.01)
 C12N 1/12     (2006.01)
 C12R 1/89     (2006.01)

(52) U.S. Cl.
 CPC ............... *C12P 7/46* (2013.01); *C12N 1/125* (2021.05); *C12P 2203/00* (2013.01); *C12R 2001/89* (2021.05)

(58) Field of Classification Search
 None
 See application file for complete search history.

(56) References Cited

U.S. PATENT DOCUMENTS

| | | |
|---|---|---|
| 9,233,906 B2 | 1/2016 | Gerberding et al. |
| 9,272,977 B2 | 3/2016 | Soper et al. |
| 2013/0102055 A1 | 4/2013 | Katz et al. |
| 2014/0178944 A1 | 6/2014 | Parekh et al. |
| 2017/0029854 A1 | 2/2017 | Del et al. |
| 2018/0305656 A1 | 10/2018 | Wendt et al. |

FOREIGN PATENT DOCUMENTS

| | | |
|---|---|---|
| CN | 101386815 A | 3/2009 |
| CN | 102476989 A | 5/2012 |
| CN | 102634442 A | 8/2012 |
| CN | 103524327 A | 1/2014 |
| CN | 104195182 A | 12/2014 |
| CN | 204933271 U | 1/2016 |
| CN | 106589103 A | 4/2017 |
| CN | 206916118 U | 1/2018 |
| CN | 109265337 A | 1/2019 |
| JP | 5130816 B2 | 1/2013 |
| KR | 10-1540520 B1 | 7/2015 |
| TW | I543809 B | 8/2016 |
| WO | 2012/127004 A1 | 9/2012 |
| WO | 2013/045931 A1 | 4/2013 |
| WO | 2013/173562 A1 | 11/2013 |

OTHER PUBLICATIONS

Wahlen et al., Mitigation of variable seasonal productivity in algae biomass through blending and ensiling, Algal Res. 42, 2019, 101584. (Year: 2019).*
Thuy et al., Production of very-high purity succinic acid from fermentation broth using microfiltration and nanofiltration-assisted crystallization, J. Membrane Sci. 524, 2017, 470-81 (Year: 2017).*
Catalanotti et al., "Fermentation metabolism and its evolution in algae", frontiers in Plant Science, vol. 4, Art 150, (May 2013), 17 pages.
Dong et al., "Impact of biochemical composition on susceptibility of algal biomass to acid-catalyzed pretreatment for sugar and lipid recovery", Algal Research 18, (Jun. 2016), pp. 69-77.
Dong et al., Diluted acid pretreatment for an integrated microalgae bio-refinery to produce lipid- and carbohydrate-based fuels, Algae Biomass Summit, Sep. 30, 2014.
Kumar et al., Recent Developments on Biofuels Production from Microalgae and Macroalgae, Renewable and Sustainable Energy Reviews 65 (2016) pp. 235-249.
Meeske, R., "Adding of a blue-green micro-algae, spirulina, to maize at ensiling", www.sasas.co.za/Popular/Popular.html, SA-ANIM SCI, vol. 5, (2004), pp. 8-10.
Murphy et al., "A perspective on algal biogas", IEA Bioenergy, (2015), 40 pages.
Wahlen et al, "Preservation of Microalgae, Lignocellulosic Biomass Blends by Ensiling to Enable Consistent Year-Round Feedstock Supply for Thermochemical Conversion to Biofuels", Frontiers in Bioengineering and Biotechnology, vol. 8, Art. 316, (Apr. 15, 2020) 9 pages.
Wirth et al., Exploitation of algal-bacterial associations in a two-stage biohydrogen and biogas generation process, Biotechnology for Biofuels (2015) 8:59.

* cited by examiner

*Primary Examiner* — Todd M Epstein
(74) *Attorney, Agent, or Firm* — TraskBritt

(57) ABSTRACT

A method of producing succinic acid from a biomass. The method comprises adding citric acid to a biomass comprising microalgae to form an acidified microalgae composition. The acidified microalgae biomass composition is stored under anaerobic conditions without inoculating the acidified microalgae composition with bacteria formulated to produce succinic acid. A coproduct comprising succinic acid is produced. Other methods of producing succinic acid from a biomass are also disclosed.

20 Claims, 5 Drawing Sheets

US 11,952,609 B2

METHODS OF PRODUCING SUCCINIC ACID FROM A BIOMASS

CROSS-REFERENCE TO RELATED APPLICATION

This application claims the benefit under 35 U.S.C. § 119(e) of U.S. Provisional Patent Application Ser. No. 63/200,311, filed Mar. 1, 2021, the disclosure of which is hereby incorporated herein in its entirety by this reference.

STATEMENT REGARDING FEDERALLY SPONSORED RESEARCH OR DEVELOPMENT

This invention was made with government support under Contract Number DE-AC07-05ID14517 awarded by the United States Department of Energy. The government has certain rights in the invention.

TECHNICAL FIELD

The disclosure, in various embodiments, relates generally to preservation of microalgae. More specifically, the disclosure, in various embodiments, relates to methods of preserving a microalgae biomass and the preserved microalgae biomass.

BACKGROUND

Algal biomass is becoming increasingly attractive as a feedstock for biofuel production and other uses. Algae have a faster growth rate and productivity than conventional terrestrial crops. The grown algae provide high-energy area yields and require less land to grow than conventional terrestrial crops. The algae can also be cultivated in fresh water, brackish water, salt water, or waste water. As with many other types of biomass, there is a seasonality to the production of the algal biomass. In many geographical areas, the production of the algal biomass may occur year-round. However, the growth rate and yield fluctuate due to changes in temperature and solar irradiation. The fluctuation in production between summer and winter months poses a challenge for delivering a predictable, constant feedstock supply to a conversion facility. During the summer months, when algal biomass productivity is highest, production may exceed conversion capacity, resulting in delayed processing. However, the algal biomass is susceptible to degradation following harvesting due to oxygen ($O_2$) and moisture exposure. Therefore, the algal biomass is ideally used immediately after harvesting. The seasonal variability and the risk of algal biomass degradation increases uncertainty in algal biomass productivity and increases risks to feedstock supply for conversion.

Drying has been used to stabilize the algal biomass for long term storage. Any algal biomass produced in excess during the high productivity summer months is dried and stored for utilization during low productivity months. However, drying is energy intensive, costly, and produces greenhouse gases.

Wet, anaerobic storage, e.g., ensiling, has been utilized to preserve many types of herbaceous biomass including corn stover, wheat straw, sweet sorghum, switchgrass, and other grasses. Ensiling is a widely used method of preserving herbaceous crops, where lactic fermentation of soluble sugars by *Lactobacillus* sp. produces organic acids (e.g., lactic acid, acetic acid), lowering the pH of the stored herbaceous biomass. The reduced pH limits further microbial degradation and stabilizes the herbaceous biomass. Ensiling has also been used to preserve macroalgae. Small quantities of microalgae (less than 2.5%) have also been added to silage in order to increase the protein content for feed or for increased yield in anaerobic digestion.

BRIEF SUMMARY

A method of producing succinic acid from a biomass is disclosed. The method comprises adding citric acid to a biomass comprising microalgae to form an acidified microalgae composition. The acidified microalgae biomass composition is stored under anaerobic conditions without inoculating the acidified microalgae composition with bacteria formulated to produce succinic acid. A coproduct comprising succinic acid is produced.

Another method of producing succinic acid from a biomass is disclosed. The method comprises adding citric acid to a biomass comprising microalgae to form an acidified microalgae composition. The acidified microalgae biomass composition is stored under anaerobic conditions and exposed to carbon dioxide, nitrogen, or a combination thereof to produce a coproduct comprising succinic acid.

DETAILED DESCRIPTION

Figures 1, 2, 3, 4:
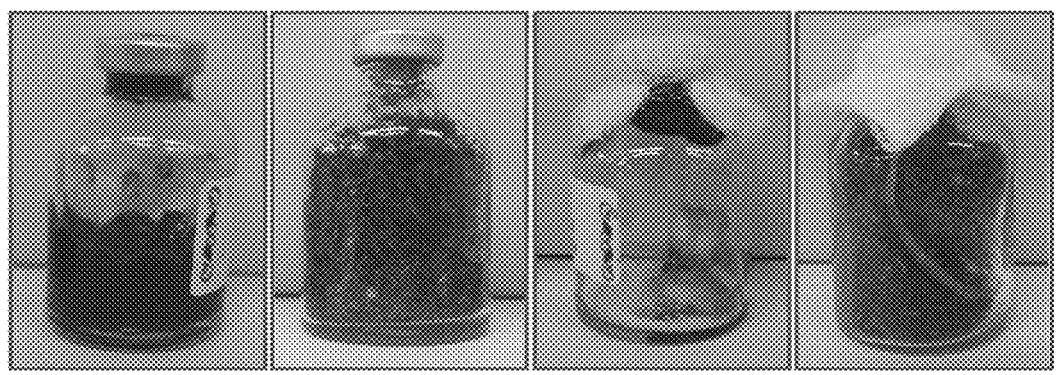
FIGS. 1-4 are photographs of samples of microalgae biomass and microalgae biomass blends treated with various acids according to embodiments of the disclosure.

Methods of preserving, e.g., stabilizing, a biomass, such as a microalgae biomass, are disclosed. The microalgae biomass is preserved using a wet storage process, which lowers the cost of preserving the microalgae biomass compared to a drying process. No drying of the microalgae biomass is utilized for the wet storage process. The wet storage process stabilizes a metabolic capacity (e.g., a potential metabolic activity) of the microalgae biomass, enabling use of the microalgae biomass months after its harvest. By preserving the microalgae biomass, the microalgae biomass may be stored during high productivity months, such as during summer months, and subsequently used as a feedstock during low productivity months. Thus, the preserved microalgae biomass may be used to meet seasonal demands for the microalgae biomass and a biorefinery that utilizes the microalgae biomass as a feedstock may be operated at about 100% capacity or close to near capacity year round. The wet storage process of the microalgae biomass may ensile the microalgae and also produces one or more commercially valuable coproducts, such as succinic acid ($(CH_2)_2(CO_2H)_2$) or other organic acid. The coproducts upgrade the microalgae biomass in addition to preserving the microalgae biomass. The microalgae biomass may be preserved and the coproducts produced concurrently utilizing the wet storage process. The coproducts may be separated and recovered. A herbaceous biomass may, optionally, be used in the wet storage process to improve the preservation of the microalgae biomass. A preserved biomass is also disclosed.

An organic acid different than the produced coproduct(s) is added to the microalgae biomass to preserve the microalgae biomass and to produce the desired coproduct(s). To distinguish from the desired coproduct(s), which may include one or more organic acids and is referred to as a coproduct organic acid, the organic acid added to the microalgae biomass is referred to herein as a preservation organic acid. The coproduct organic acid may be produced when an acidified microalgae biomass composition is stored and maintained under anaerobic conditions. The preservation organic acid added to the microalgae biomass is a water-soluble compound having a relatively low molecular weight. Appropriate selection of the preservation organic acid enables a desired metabolic function to be selected for in the microalgae biomass, rather than needing to inoculate the microalgae biomass with a strain of microorganism that exhibits the desired metabolic function. Use of the preservation organic acid may enable the desired coproduct organic acids to be produced at a greater than expected yield even though the desired coproduct(s) are not a metabolic function of organisms of the microalgae biomass. The methods according to embodiments of the disclosure produce the coproduct organic acid(s) at relatively greater amounts compared to the production when no preservation organic acid is added to the microalgae biomass.

As used herein, the term "microalgae" means and includes unicellular, eukaryotic organisms or cyanobacteria that are capable of photoautotrophic growth where solar energy is used to fix carbon dioxide ($CO_2$) into organic compounds (e.g., sugars) with the concomitant release of oxygen ($O_2$). The microalgae may be a naturally occurring species, a genetically selected strain, a genetically manipulated strain, a transgenic strain, a synthetic microalgae, or combinations thereof. The microalgae may include, but is not limited to, green algae, brown algae, red algae, or combinations thereof. The microalgae may include a single species or strain of microalgae, or a combination of species or strains, such as those grown in a polyculture. By way of example only, the microalgae may include, but is not limited to, *Chlorella, Spirulina, Phaeophyta, Coelastrum, Micractinium, Nannochloropsis, Porphyridium, Nostoc, Haematococcus, Chlorophyta, Rhodophyta, Dunaliella, Scenedesmus, Microcystis, Synechocystis, Anabaena, Chlamydomonas, Oedogonium*, or combinations thereof. In some embodiments, the microalgae are *Scenedesmus*, such as *Scenedesmus obliquus* (also known as Tetradesmus obliquus UTEX 393) or *Scenedesmus acutus*.

As used herein, the term "biomass" means and includes a biological material that can be converted into a biofuel, chemical, or other product.

As used herein, the term "herbaceous" means and includes a cellulosic biomass that contains sugar polymers and lignin and may be at low or high moisture content. The herbaceous biomass may be derived from an agricultural crop, crop residue, trees, woodchips, sawdust, paper, cardboard, grasses, yard waste, or combinations thereof. The herbaceous biomass may include, but is not limited to, corn stover, grass clippings, grain sorghum residue, biomass sorghum, or combinations thereof.

As used herein, the term "preserved" or "stabilized" means and includes maintaining the metabolic capacity of the microalgae biomass or microalgae biomass blend without substantially degrading the microalgae biomass or microalgae biomass blend. For instance, the metabolic capacity of the microalgae biomass may be stabilized for at least one week, such as at least two weeks, while exhibiting a dry matter loss of less than about 30% dry basis (db), such as less than about 25% dry basis, less than about 20% dry basis, less than about 15% dry basis, less than about 10% dry basis, less than about 5% dry basis, or less than about 2% dry basis. The metabolic capacity of the microalgae biomass may include, but is not limited to, cellular respiration or turnover of energy sources, e.g., carbohydrates, lipids, proteins, or combinations thereof. By way of example only, the metabolic capacity of the microalgae biomass may be stabilized for one month or more, two months or more, three months or more, four months or more, five months or more, or six months or more, while exhibiting a dry matter loss of less than about 15% dry basis. In some embodiments, the loss in dry matter may be less than about 10% dry basis, less than about 5% dry basis, or less than about 2% dry basis.

As used herein, the term "anaerobic" means and includes an amount of oxygen in an environment that is less than about 10% of saturation for dissolved oxygen. By way of example only, the amount of oxygen may be less than about 5% of saturation for dissolved oxygen, less than about 4% of saturation for dissolved oxygen, less than about 3% of saturation for dissolved oxygen, less than about 2% of saturation for dissolved oxygen, or less than about 1% of saturation for dissolved oxygen.

The preserved microalgae biomass including the one or more coproduct organic acids, such as succinic acid, may improve the process of producing and converting the microalgae biomass to a biofuel. The preserved microalgae biomass may be used as a feedstock for a bioprocess, e.g., a fuel conversion technology, such as hydrothermal liquefaction for microalgae or microalgae/herbaceous biomass blends conversion, algal lipid extraction and upgrading, and carbohydrate/protein microbial fermentation followed by hydrothermal liquefaction. By way of example only, the succinic acid produced during methods according to embodiments of the disclosure may be used as a precursor in the production of biofuel. The conversion of the preserved microalgae biomass into the biofuel may be conducted in the biorefinery by conventional techniques, which are not described in detail herein. By preserving the microalgae biomass, the feedstock supply chain may be consistent and the risk of running the biorefinery at less than full capacity is reduced. The preserved microalgae biomass may be easily transported from its harvest site and stored until use at an on-site storage facility located in proximity to the biorefinery or used at a centrally located biorefinery. By including a low cost herbaceous biomass, such as yard waste, with the microalgae biomass, a low cost feedstock for the bioprocess may be produced. The preserved microalgae biomass may also be used as fodder or feed for livestock. By tailoring the ratio of microalgae biomass to herbaceous biomass, the protein content of the fodder or feed may be optimized.

Since the process is a wet process, less water removal is needed, decreasing the cost of the process, the energy used in the process, and greenhouse gas emissions. The wet storage process of the disclosure may preserve the metabolic capacity of the microalgae biomass without substantial dry matter loss. The metabolic capacity of the microalgae biomass or microalgae biomass blend may remain substantially the same before and after the addition of the preservation organic acid. In other words, the addition of the preservation organic acid does not decrease the potential for the microalgae biomass or microalgae biomass blend to produce the desired coproduct(s). The wet storage process of the disclosure may, thus, extend the storage period for the microalgae biomass, such as up to six or more months compared to days without preserving the microalgae biomass. In some embodiments, the wet storage process of the disclosure preserves the metabolic capacity of the microalgae biomass for at least about 30 days (e.g., about one month), with a dry matter loss of less than about 15% dry basis (db) during the storage period. The wet storage process of the disclosure may enable shorter term preservation of the microalgae biomass during formation of the coproduct(s), such as for about one week or about two weeks.

The microalgae biomass may be produced and harvested by conventional techniques, which are not described in detail herein. After harvesting, the microalgae biomass may be chopped or comminuted into smaller pieces. The harvested microalgae biomass may have a neutral pH, such as a pH of about 7.0 or greater, a pH of about 8.0 or greater, or a pH of from about 7.0 to about 8.0. The microalgae biomass may, optionally, be concentrated, e.g., water removed, before use in the wet storage process. The concentrated microalgae biomass includes solids and may have a moisture content of from about 50% wet basis (wb) to about 90% (wb), such as a moisture content of from about 60% wet basis to about 80% wet basis. The moisture content is determined by drying to a constant weight at 105° C. In some embodiments, the concentrated microalgae biomass has a paste-like consistency and a solids content of about 20%, which is conventional for microalgae biomass that is to be converted into a fuel, such as a biofuel. However, the concentrated microalgae biomass may have a higher solids content or a lower solids content. In some embodiments, the moisture content of the concentrated microalgae biomass is about 80% wet basis.

Before preserving the microalgae biomass, at least one herbaceous biomass may, optionally, be combined with the microalgae biomass. The herbaceous biomass may be produced and harvested by conventional techniques, which are not described in detail herein. For convenience and simplicity, the term "microalgae biomass blend" is used herein to refer to a biomass having the microalgae biomass and the at least one herbaceous biomass. The microalgae biomass or the microalgae biomass blend may be preserved using the wet storage process according to embodiments of the disclosure. While specific embodiments herein describe a blend of microalgae and corn stover, another herbaceous biomass may be used in place of the corn stover. The ratio of the microalgae biomass to the herbaceous biomass in the microalgae biomass blend may range from about 5% dry basis (db) to about 40% db of the microalgae biomass: from about 60% db to about 95% db of the herbaceous biomass. The ratio of the microalgae biomass to the herbaceous biomass may be tailored depending on the desired use of the preserved microalgae biomass blend. In some embodiments, the ratio of the microalgae biomass to the herbaceous biomass in the microalgae biomass blend is about 20% db:about 80% db. The herbaceous biomass may be combined with the microalgae biomass, such as by simple mixing, before preserving the microalgae biomass blend. By way of example only, if the herbaceous biomass is a dry solid, the herbaceous biomass may be rehydrated with water prior to combining the herbaceous biomass and microalgae biomass. The microalgae biomass blend may have a moisture content of from about 50% wet basis to about 90% wet basis, such as a moisture content of from about 60% wet basis to about 80% wet basis. The microalgae biomass and the herbaceous biomass may be combined in a vessel in which the wet storage process is to be conducted.

In some embodiments, the microalgae biomass or microalgae biomass blend includes *Scenedesmus obliquus*. While *Scenedesmus obliquus* may produce succinic acid, such as during the citric acid cycle or other metabolic processes, the succinic acid produced by the organism does not accumulate in the organism. Rather, any succinic acid that is produced is utilized in a subsequent stage of the citric acid cycle or other metabolic process.

The microalgae biomass or microalgae biomass blend may be preserved from immediately after harvesting up until about 72 hours after harvesting. To preserve the microalgae biomass or microalgae biomass blend, the microalgae biomass or microalgae biomass blend may be acidified, such as by adding an acid, acid salt, or an acid source compound to the microalgae biomass or microalgae biomass blend. The acid may be an organic acid or an inorganic acid, the acid salt may be an organic acid salt or an inorganic acid salt, such as sodium bisulfate or sodium sulfate, and the acid source compound may be an organic acid source compound or an inorganic acid source compound. The preservation organic acid may be lactic acid, acetic acid, sulfuric acid, formic acid, propionic acid, citric acid, benzoic acid, hexanoic acid, succinic acid, or combinations thereof. In some embodiments, the preservation organic acid is citric acid. The acid source compound may be a chemical compound that reacts with another compound in the microalgae biomass or microalgae biomass blend to produce one of the above-mentioned preservation organic acids. The microalgae biomass or microalgae biomass blend may be contacted with the preservation organic acid or acid source compound, such as by adding a preservation organic acid solution to a vessel containing the microalgae biomass or microalgae biomass blend. The preservation organic acid solution may be an aqueous solution of the acid, of the acid salt, or of the acid source compound. The pH of the preservation organic acid solution may range from about 1.0 to about 5.0, such as from about 1.0 to about 4.0, from about 1.0 to about 3.0, from about 2.0 to about 4.0, from about 3.0 to about 5.0, or from about 1.0 to about 2.0. In some embodiments, the pH of the preservation organic acid solution is about 2.0. In other embodiments, the pH of the acid solution is about 4.0. In other embodiments, the pH of the acid solution is about 5.0.

A sufficient volume of the preservation organic acid solution may be added to the microalgae biomass or the microalgae biomass blend to produce an acidified microalgae biomass composition having the desired pH and a moisture content of from about 50% wet basis to about 90% wet basis. The preservation organic acid may be added to the microalgae biomass or to the microalgae biomass blend at between about 1% db and about 5% db, such as between about 1% db and about 3% db, between about 3% db and about 5% db, between about 2% db and about 5% db, between about 3% db and about 7% db, or between about 4% db and about 6% db. It is understood that the acidified microalgae biomass composition may include the microalgae biomass or the microalgae biomass blend. The addition of the preservation organic acid solution may reduce the pH of the acidified microalgae biomass composition to less than about 7.0. The preservation organic acid solution may be added to the microalgae biomass or the microalgae biomass blend such that the pH of the acidified microalgae biomass composition is less than about 7.0, such as less than about 6.0, less than about 5.0, less than about 4.0, less than about 3.0, less than about 2.0, or less than about 1.0. The pH of the acidified microalgae biomass composition may be from about 1.0 to about 6.0, from about 1.0 to about 5.0, from about 1.0 to about 4.0, from about 1.0 to about 3.0, from about 2.0 to about 4.0, from about 2.0 to about 5.0, from about 3.0 to about 5.0, from about 1.0 to about 2.0, from about 1.5 to about 4.5, from about 1.5 to about 3.5, from about 1.5 to about 2.5, from about 2.0 to about 4.0, from about 2.5 to about 4.5, from about 3.0 to about 4.0, or from about 4.0 to about 5.0. Upon reaching the desired pH, growth of microorganisms, such as bacteria, mold, and yeast, in the microalgae biomass or microalgae biomass blend may be inhibited and the microalgae biomass or microalgae biomass blend is preserved. In some embodiments, the pH of the acidified microalgae biomass composition is between about 2.0 and about 3.0. In other embodiments, the pH of the acidified microalgae biomass composition is between about 3.0 and about 4.0. In yet other embodiments, the pH of the acidified microalgae biomass composition is between about 4.0 and about 5.0. The pH of the acidified microalgae biomass composition may be maintained in this range for about one month or more. In some embodiments, the acid solution is added to the microalgae biomass or the microalgae biomass blend to achieve a moisture content of about 60% wet basis. The vessel in which the microalgae biomass or microalgae biomass blend is acidified may be a conventional reactor, which is not described in detail herein.

The addition of the preservation organic acid may also improve (e.g., decrease) the dry matter loss of the microalgae biomass. By way of example only, the preserved microalgae biomass or the preserved microalgae biomass blend may exhibit a dry matter loss of less than about 1% db during a 24 hour time period. In comparison, a microalgae biomass that has not been preserved by the addition of the preservation organic acid may exhibit a dry matter loss of about 4% db during a 4 hour time period. The metabolic capacity of the acidified microalgae biomass or the acidified microalgae biomass blend may be from about 90% to about 100% of the metabolic capacity of the initial microalgae biomass or initial microalgae biomass blend, such as from about 92% to about 100% of the metabolic capacity of the initial microalgae biomass or initial microalgae biomass blend, from about 95% to about 100% of the metabolic capacity of the initial microalgae biomass or initial microalgae biomass blend, or from about 98% to about 100% of the metabolic capacity of the initial microalgae biomass or initial microalgae biomass blend.

The treatment with the preservation organic acid of the microalgae biomass or microalgae biomass blend may unexpectedly improve protein preservation during storage. In contrast, untreated microalgae biomass is believed to metabolize proteins to generate free amino acids, which may be used as an energy source. If, for example, the preservation organic acid is citric acid, the acidified microalgae biomass may retain a protein content. Without being bound to any theory, adding the preservation organic acid according to embodiments of the disclosure is believed to alter the metabolic activity of the microalgae biomass, including protein metabolism. In some embodiments, treatment with the preservation organic acid may enable the microalgae biomass to retain from about 50% db protein content to about 95% db protein content, from about 60% db protein content to about 90% db protein content, from about 70% db protein content to about 90% db protein content, or from about 80% db protein content to about 95% db protein content relative to the initial mass of the microalgae biomass or initial microalgae biomass blend.

After acidification with the preservation organic acid, the acidified microalgae biomass composition may be stored and maintained in the vessel under anaerobic conditions, during which time the coproduct organic acids are produced. By way of example only, the vessel containing the acidified microalgae biomass composition may be sealed and purged to remove air, preventing exposure of the acidified microalgae biomass composition to oxygen ($O_2$). The vessel may also contain sufficient biomass such that limited airspace is remaining in the vessel. A sufficient volume of the acidified microalgae biomass composition may be added to the vessel with mechanical compaction to achieve the limited airspace in the vessel. The acidified microalgae biomass composition may be purged with carbon dioxide, nitrogen, or combinations thereof. In some embodiments, carbon dioxide is used to purge the acidified microalgae biomass composition. The vessel may be stored at room temperature (from about 20° C. to about 25° C.) and in the dark for the desired storage period. The vessel in which the acidified microalgae biomass composition is stored and maintained under anaerobic conditions may be the same as or different from the vessel in which the microalgae biomass or microalgae biomass blend is acidified.

The coproduct organic acid may be produced as the acidified microalgae biomass composition is stored and maintained under the anaerobic conditions. The carbon dioxide, nitrogen, or combinations thereof introduced into the vessel may produce the coproduct (e.g., the one or more desired coproduct organic acids) during storage of the acidified microalgae biomass composition, which includes the microalgae biomass or microalgae biomass blend. The coproduct may be a commercially valuable coproduct that increases the value of the preserved microalgae biomass or microalgae biomass blend. The coproduct may be a specialty chemical compound, such as a precursor used in a pharmaceutical, nutraceutical, or other industry. These coproducts can be precursors to other fuel products and offer a valuable coproduct stream for biorefineries. The coproduct may be a solid, liquid, or a gas. The solid or liquid coproduct may be an organic acid including, but not limited to, succinic acid, butanediol, lactic acid, acetic acid, propionic acid, butyric acid, glycerol, ethanol, or combinations thereof. If the desired coproduct is an organic acid, the coproduct organic acid differs from the preservation organic acid. By way of example only, the coproduct organic acid has a different chemical formula or a different chemical structure than the preservation organic acid. By way of example only, the coproduct organic acid may differ in one or more of the number of carbon atoms, the number of hydrogen atoms, the number of oxygen atoms, or number (e.g., degree) of unsaturations. In some embodiments, the coproduct is succinic acid. The gaseous coproduct may include, but is not limited to, hydrogen, methane, or a combination thereof. By way of example only, when the acidified microalgae biomass is stored alone, the anaerobic metabolism may produce succinic acid, butanediol, lactic acid, acetic acid, propionic acid, butyric acid, glycerol, ethanol, or combinations thereof.

The introduction of the carbon dioxide, nitrogen, or a combination thereof into the vessel containing the acidified microalgae biomass composition may further increase the amount of succinic acid or other coproduct produced during the wet storage process compared to conducting the wet storage process without the introduction of the carbon dioxide, nitrogen, or a combination thereof. In addition to succinic acid, acetic acid, propionic acid, lactic acid, butyric acid, or a combination thereof may be produced. Thus, the preserved microalgae biomass or preserved microalgae biomass blend may include higher amounts of the succinic acid or other coproducts than were present in the microalgae biomass or microalgae biomass blend before conducting the wet storage process. The increased succinic acid yield according to embodiments of the disclosure may be significantly greater than the amount of succinic acid produced by metabolic processes of the microalgae. The production of succinic acid or other coproducts was unexpected and surprising since no succinic acid fermentative bacteria (e.g., *Actinobacillus succinogenes*) inoculation was conducted during the wet storage process. In some embodiments, the succinic acid is present in the preserved microalgae biomass or preserved microalgae biomass blend at up to 14% on a dry weight basis. In other embodiments, the succinic acid is present in the preserved microalgae biomass or preserved microalgae biomass blend at up to 45% on a dry weight basis.

The coproduct, such as succinic acid, may also be produced when the acidified microalgae biomass composition is stored and maintained under the anaerobic conditions where the vessel has a headspace above the acidified microalgae biomass composition. The headspace may provide a sufficient volume for the microalgae biomass to expand in volume during the wet storage process. The headspace may be produced by introducing a desired volume of the acidified microalgae biomass composition into the vessel to partially fill the vessel and then evacuating the vessel. Alternatively, the headspace may be produced by partially filling the vessel with the desired volume of the acidified microalgae biomass composition and then introducing $CO_2$ or nitrogen into the vessel. Without being bound to any theory, it is believed that as the microalgae biomass of the acidified microalgae biomass composition degrades, $CO_2$ is produced, which $CO_2$ is subsequently consumed by the microalgae to produce the coproduct, such as the succinic acid. To produce the coproduct, the acidified microalgae biomass composition may be stored in the vessel having headspace under the anaerobic conditions and in an environment comprising $CO_2$, consisting essentially of $CO_2$, or consisting of $CO_2$. This environment in the vessel may be maintained by preventing air infiltration into the vessel.

The acidified microalgae biomass composition may be stored under the carbon dioxide, nitrogen, or a combination thereof for an amount of time sufficient to produce the succinic acid or other coproduct without experiencing significant dry matter loss of the microalgae biomass or the microalgae biomass blend or a decrease in the metabolic capacity of the microalgae biomass or the microalgae biomass blend. In some embodiments, the acidified microalgae biomass composition is purged with carbon dioxide. The wet storage process of the disclosure may preserve the metabolic capacity of the microalgae biomass without substantial dry matter loss, such as less than about 15% dry basis over the storage period. In some embodiments, the dry matter loss is less than about 10% dry basis over the storage period, less than about 5% dry basis over the storage period, or less than about 2% dry basis over the storage period. The carbon dioxide, nitrogen, or a combination thereof may be maintained in the vessel until a maximum amount of the coproduct is produced without experiencing a significant loss of the dry matter or a decrease in the metabolic capacity of the microalgae biomass or of the microalgae biomass blend. In some embodiments, the wet storage process of the disclosure enables the microalgae biomass or the microalgae biomass blend to be stored for up to about six months or more. The wet storage process of the disclosure preserves the metabolic capacity of the microalgae biomass or the microalgae biomass blend for at least about 30 days, with less than about 5% dry matter loss.

Without being bound to any theory, it is believed that introducing the $CO_2$ enables the production of the succinic acid. Since the microalgae biomass remains metabolically active during the wet storage process, sugars, carbohydrates, proteins, lipids, or combinations thereof present in the acidified microalgae biomass composition may be converted to succinic acid. By way of example only, glucose in the acidified microalgae biomass composition may be converted to succinic acid by way of pyruvate carboxylase or phosphoenolpyruvate carboxykinase and the reductive branch of the citric acid cycle (i.e., the Krebs cycle or tricarboxylic acid (TCA) cycle). Thus, the succinic acid is produced in-situ from the microalgae biomass or microalgae biomass blend following the addition of the preservation organic acid. In other words, the succinic acid produced as the coproduct organic acid differs from the preservation organic acid initially added to the microalgae biomass or the microalgae biomass blend. It was surprising and unexpected that the succinic acid was produced in-situ since no succinic acid was used as the preservation organic acid to acidify the microalgae biomass or the microalgae biomass blend and no succinic acid fermentative bacteria (e.g., *Actinobacillus succinogenes*) inoculation was conducted. The methods according to embodiments of the disclosure produce the coproduct organic acid(s), such as succinic acid, at greater relative amounts compared to the production when no preservation organic acid is added to the microalgae biomass. In some embodiments, the produced succinic acid is at almost one-half the weight of the dry biomass. By way of example only, the succinic acid may be produced at up to 45% db compared to about 5% db when no preservation organic acid is added to the microalgae biomass.

The treatment with the preservation organic acid may alter protein expression in the acidified microalgae biomass during storage. If, for example, the preservation organic acid is citric acid, an unexpected decrease in the upregulation of the glycolysis pathway in the acidified microalgae biomass or acidified microalgae biomass blend may occur. Under anaerobic conditions, anaerobic glycolysis is expected to occur in cellular respiration as a mechanism for energy metabolism. In some embodiments, the expression of the gluconeogenesis proteins, phosphoenolpyruvate carboxykinase (PEPCK) and malate dehydrogenase (MDH), may be unexpectedly upregulated. For example, under anaerobic conditions and in the absence of the preservation organic acid, the microalgal biomass is expected to metabolize glucose rather than generate new glucose.

Without being bound by any theory, it is believed that the addition of the preservation organic acid, such as citric acid, allows the degradation of proteins that may increase the presence of TCA cycle intermediates, such as succinic acid. The TCA cycle intermediates may be used to generate ATP while being converted to oxaloacetate. The oxaloacetate is believed to be converted into phosphoenolpyruvate via PEPCK, which decarboxylates and phosphorylates oxaloacetate from the TCA cycle. In the absence of the preservation organic acid, the phosphoenolpyruvate formed during glycolysis is believed to undergo substrate level phosphorylation of ADP to form ATP and pyruvate via pyruvate kinase (PK), where expressed PK levels may be increased in untreated microalgae biomass as compared to the acidified microalgae biomass. The PK expression levels may remain relatively constant in the acidified microalgae biomass. It is also believed that citric acid may inhibit or repress expression of PEPCK and MDH.

By way of example only, if citric acid is used as the preservation organic acid and is added to the microalgae biomass, an unexpected amount (e.g., concentration) of succinic acid may be produced as the coproduct organic acid even though no succinic acid is added to the microalgae biomass and the formation of succinic acid by metabolic processes does not accumulate in the microalgae biomass. Succinic acid may be produced as the coproduct organic acid without inoculating the microalgae biomass with a bacteria having a metabolic process that includes succinic acid formation. The total coproduct organic acids may be produced at up to about 40% dry basis of the total biomass. The total coproduct organic acids may be produced at from about 20% db to about 40% db, such as from about 20% db to about 30% db, from about 20% db to about 35% db, from about 25% db to about 40% db, from about 25% db to about 35% db, from about 30% db to about 35% db, from about 30% db to about 50% db, or from about 35% db to about 45% db. In some embodiments, greater than or equal to about 20% succinic acid db is present, such as from about 20% db to about 35% db succinic acid, from about 20% db to about 30% db succinic acid, from about 25% db to about 35% db succinic acid, or from about 25% db to about 30% db succinic acid, from about 30% db to about 50% db, or from about 35% db to about 45% db. By comparison, if no citric acid (as the preservation organic acid) is added to the microalgae biomass (e.g., untreated microalgae biomass), the untreated microalgae biomass may produce acetic, propionic and butyric acids as the predominant coproduct organic acids at organic acid concentrations of about 10% of the total biomass db. Without being bound to any theory, it is believed that the citric acid addition may produce the high concentration of succinic acid as a result of algae anaerobic metabolism.

If, however, succinic acid is used to acidify the microalgae biomass or the microalgae biomass blend (i.e., as the preservation organic acid), an increased amount of succinic acid is present following the conversion relative to the amount of succinic acid used to acidify the microalgae biomass or the microalgae biomass blend. While lactic acid has been produced from macroalgae (i.e., seaweed) biomass, inoculating the macroalgae biomass with lactic acid bacteria (LAB) was required because the macroalgae are not metabolically active after harvesting. Therefore, although lactic acid is produced, the lactic acid is not produced in-situ by the macroalgae biomass. Rather, the macroalgae biomass requires the LAB inoculation to produce the lactic acid.

The succinic acid formation as the coproduct organic acid may retain carbon in the microalgae biomass, minimizing loss as carbon dioxide. Furthermore, succinic acid present in the microalgae biomass may enhance the production of some products, since succinic acid may function as a substrate in some biochemical processes and be readily assimilated into products (e.g., butanediol, polybutylene succinate). As a metabolite of the citric acid cycle, succinic acid is also readily metabolized in aerobic conditions, providing energy and carbon for product formation. Due to market value and its accumulation in storage at a high titer, the succinic acid or other coproduct organic acid may be recovered.

The coproduct organic acid may then be recovered from the acidified microalgae biomass composition including the microalgae biomass or microalgae biomass blend. If the coproduct is a solid or liquid, the coproduct may be recovered by conventional separation techniques including, but not limited to, filtration, crystallization, decantation, sublimation, evaporation, simple distillation, fractional distillation, extraction, or chromatography. If the coproduct is gaseous, the coproduct may be recovered by enabling the gaseous coproduct to be selectively removed from the vessel. The wet storage process according to embodiments of the disclosure may produce the coproduct at a yield of up to about 0.34 g of coproduct per gram of sugar, carbohydrate, protein, or lipid present in the microalgae biomass or microalgae biomass blend. By way of example only, succinic acid may be produced at up to about 14% on a dry weight basis (i.e., up to about 14% succinic acid per gram of microalgae biomass), such as from about 6% on a dry weight basis to about 14% on a dry weight basis. For instance, when the vessel includes a headspace during the wet storage process, up to about 10% by weight of the succinic acid may be produced. By recovering the commercially valuable coproduct, the coproduct may be sold to offset costs of the wet storage process, such as storage cost. In some embodiments, the coproduct is succinic acid, which is a precursor for multiple, high-value commodity chemicals.

The coproduct organic acid may be recovered from the acidified microalgae biomass composition by a separation (e.g., filtration, microfiltration, nanofiltration) process, such as a membrane separation process. A membrane of the membrane separation process may be selected based on properties of the desired coproduct organic acid, such as molecular weight. The membrane may be a microfiltration membrane or a nanofiltration membrane selected to exhibit a high degree of selectivity and permeability for the coproduct organic acid and be compatible with the harsh environment of the acidified microalgae biomass composition. The membrane may be in the form of a coupon or module. By way of example only, the membrane may be a polymeric membrane, such as a microfiltration membrane or a nanofiltration membrane. If the coproduct organic acid to be recovered is succinic acid, the membrane may have a molecular weight cutoff of about 90 amu.

The acidified microalgae biomass composition may be diluted, such as with water, to form a solution of the acidified microalgae biomass composition. The acidified microalgae biomass solution includes the desired coproduct organic acid, which is separated and recovered by conducting one or more filtration acts, such as one or more microfiltration acts, one or more nanofiltration acts, or a combination thereof. The coproduct organic acid may, for example, be recovered from the acidified microalgae biomass solution as a coproduct stream that includes one or more organic acid. The coproduct organic acid may be referred to herein as a biobased organic acid and the coproduct stream may be referred to herein as a biobased organic acid stream. The filtration process may include conducting multiple filtration acts to separate and recover the coproduct organic acid from other components of the acidified microalgae biomass solution. The coproduct organic acid may be recovered with a high degree of selectivity and permeability.

A microfiltration act may be conducted to separate solids from the acidified microalgae biomass solution, which includes the coproduct organic acid(s). The separated solids may be recovered and used in downstream conversion processes. A microfiltration membrane used in the microfiltration act may be selected based on the coproduct organic acid to be separated. For example, the microfiltration membrane may be selected depending on the molecular weight of the coproduct organic acid to be recovered from the acidified microalgae biomass solution. The microfiltration process may utilize a microfiltration membrane configured to separate compounds having a molecular weight cutoff similar to that of the coproduct organic acid of interest. The coproduct organic acid may be present in a liquid (e.g., a permeate) following the microfiltration act. In addition to the coproduct organic acid, the permeate may include other water-soluble components of the acidified microalgae biomass solution.

A nanofiltration process may be conducted on the permeate from the microfiltered, acidified microalgae biomass solution to further separate the coproduct organic acid(s) from the other water-soluble components. The nanofiltration process may utilize a nanofiltration membrane configured to separate compounds having a molecular weight cutoff similar to that of the coproduct organic acid of interest. The coproduct organic acids may be separated as a single stream that contains multiple coproduct organic acids from the filtered, acidified microalgae biomass solution or a single organic acid may be separated from the filtered, acidified microalgae biomass solution by appropriately selecting the nanofiltration membrane. The coproduct organic acids may be recovered in solution or as a solid.

The recovered coproduct organic acid may be used as a precursor in a biofuel process, where the one or more coproduct organic acids, such as succinic acid, may be converted into a biofuel. Water recovered from the filtration process may be recovered and reused, such as to dilute the acidified microalgae biomass composition and form the acidified microalgae biomass solution in a subsequent process stage.

The separation and recovery of the coproduct organic acid may be decoupled from the preservation of the microalgae biomass, increasing commercial interest to industries outside the microalgae biomass industry. The coproduct stream may be recovered by a filtration process that is cost effective and relatively easy. In some embodiments, the coproduct organic acid may be recovered at greater than about 85% of the organic acids possible. In addition to the filtration acts separating the organic acids, solids from the preserved microalgae biomass are retained for downstream conversion processes. The filtration acts also concentrate the coproduct organic acids.

Without being bound to any theory, it is believed that the limited oxygen during the wet storage process enables anaerobic fermentation of sugars, carbohydrates, proteins, or lipids present in the acidified microalgae biomass composition into the coproduct(s), such as the organic acid(s). The presence of the organic acid decreases the pH of the environment, limits microbial degradation, and stabilizes the microalgae biomass or the microalgae biomass blend. The produced organic acid(s) may include, but is not limited to, acetic acid, propionic acid, lactic acid, succinic acid, or butyric acid. The organic acid produced by the wet storage process may decrease the pH of the acidified microalgae biomass composition beyond the pH achieved by the addition of the acid solution to the microalgae biomass or the microalgae biomass blend. The organic acid maintains the acidic pH and serves to inhibit the growth of microorganisms responsible for excessive degradation of the microalgae biomass, including yeast, mold, and bacteria (e.g., *Clostridium* sp.).

Without being bound to any theory, it is believed that sugars, carbohydrates, proteins, or lipids present in the herbaceous biomass may increase anaerobic fermentation when used in combination with the microalgae biomass. Additionally, including the herbaceous biomass with the microalgae biomass is advantageous because rheological properties of the herbaceous biomass are maintained such that conventional apparatus and technologies for herbaceous biomass may be utilized with the microalgae biomass blend. By way of example only, conventional storage structures ranging from small-scale silage bags to bunkers and drive over piles may be used in the wet storage process according to embodiments of the disclosure.

The preserved microalgae biomass or preserved microalgae biomass blend may be stored for one month or more, such as two months or more, three months or more, four months or more, five months or more, or six months or more, without experiencing high levels of dry matter loss. The metabolic capacity of the preserved microalgae biomass or preserved microalgae biomass blend may be maintained during the storage period, while low levels of dry matter loss are observed. The preserved microalgae biomass or preserved microalgae biomass blend may exhibit a dry matter loss of less than about 15% dry basis during storage, such as from about 6.5% dry basis to about 14.5% dry basis. In comparison, control microalgae biomass compositions that were not acidified but were stored under anaerobic conditions exhibited a dry matter loss of about 37% dry basis during storage. Control microalgae biomass compositions that were not acidified and were stored under aerobic conditions also exhibited a greater dry matter loss than the acidified microalgae biomass compositions. The microalgae biomass or microalgae biomass blend acidified with acetic acid and lactic acid exhibited a dry matter loss of from about 6.8% dry basis to about 8.8% dry basis, while the microalgae biomass or microalgae biomass blend acidified with sulfuric acid exhibited a dry matter loss of from about 12% dry basis to about 14% dry basis.

To further increase the preservation of the microalgae biomass or microalgae biomass blend, the acidified microalgae biomass composition may, optionally, be inoculated with bacteria, such as lactic acid bacteria (LAB), before storing the acidified microalgae biomass composition under the anaerobic conditions. However, the wet storage process according to embodiments of the disclosure may be conducted without an LAB, or other bacteria, inoculation.

The following examples serve to explain embodiments of the disclosure in more detail. These examples are not to be construed as being exhaustive or exclusive as to the scope of the disclosure.

EXAMPLES

Example 1

Scenedesmus Biomass

*Scenedesmus obliquus* was cultivated in 1,000 L outdoor raceway ponds at the Regional Algal Feedstock Testbed located at the University of Arizona in Tucson, AZ The media contained 0.134 g/L $NaNO_3$; 0.075 g/L $MgSO_4$ ($7H_2O$); 0.013 g/L $KH_2PO_4$; 0.175 g/L potash; 0.0054 g/L Fecitraplex; 0.0029 g/L $H_3BO_3$; 0.0018 g/L $MnCl_2$ ($4H_2O$); 0.0014 g/L $ZnSO_4$ ($7H_2O$): 0.0004 g/L $Na_2MoO_4$ ($2H_2O$); 0.00008 g/L $CuSO_4$ ($5H_2O$); 0.00006 g/L $Co(NO_3)_2$ ($6H_2O$); and 0.0001 g/L $NiCl_2$ ($6H_2O$). The pH of the feedstock was maintained at 8.0 with $CO_2$ injection. The microalgae biomass was concentrated by centrifugation (Evodos 10, Raamsdonksveer, The Netherlands) to a paste with a moisture content of 80% wet basis (wb), as determined by drying to a constant weight at 105° C. The algae biomass was transported overnight to the Idaho National Laboratory in a cooler on ice. The microalgae biomass was immediately used for experiments upon arrival.

Example 2

Corn Stover Biomass

Single pass corn stover was collected in Boone County, IA and was ground to pass through a 1-inch sieve using a Vermeer BG480 grinder (Pella, IA) and a Bliss Hammermill (Ponca City, OK) with no screen. In preparation for storage experiments, the corn stover was further size reduced to pass through a 6-mm screen with a Wiley Mill (model 4, Thomas, Swedesboro, NJ).

Example 3

Microalgae/Corn Stover Biomass Blend

Prior to blending, the dried corn stover was rehydrated for 24 hours with sufficient water to result in a 20:80 (dry basis, db) algae to corn stover blend with 60% moisture. At blending, sucrose was added to a concentration of 2% db of the total biomass to simulate soluble sugars that would be present in freshly chopped corn stover.

Example 4

Storage, Dry Matter Loss, and pH Experiments

The effect of acid was examined by treating the microalgae biomass and microalgae biomass blend described above with various acids. Storage experiments were conducted with microalgae/corn stover blends and with microalgae unblended as a control. Initial proof-of-principle experiments were conducted in 50 mL serum vials, where the microalgae biomass was blended with the corn stover biomass at a ratio of 20:80 (dry basis, db) microalgae to corn stover. The microalgae/corn stover blends were acidified with one of three acids or with a combination of acids (sulfuric acid, pH 4, sulfuric acid pH 2, 3% lactic acid, 5% lactic acid, a mixture of 1% acetic acid and 3% lactic acid, a mixture of 2% acetic acid and 6% lactic acid) to reach a moisture content of 60% (wb) and desired pH or acid concentration (% of dry biomass). The biomass samples were treated to simulate storage conditions typical of homolactic fermentation and heterolactic fermentation. Homolactic fermentation occurs when the primary fermentation product is lactic acid, whereas heterolactic fermentation involves the production of acetic acid and carbon dioxide in addition to lactic acid. The sulfuric acid was used to evaluate storage performance at low pH in the absence of added organic acids.

Once blended and acidified, 5 g of the microalgae biomass blends and 2 g of microalgae biomass alone were immediately transferred to 50 ml serum vials, capped with butyl rubber stoppers and aluminum seals, purged with high purity nitrogen gas for 10 minutes, and stored at room temperature for 30 days. Anaerobic controls for the microalgae biomass blends and the microalgae biomass alone were prepared in like manner without acidification. Aerobic controls for both the microalgae biomass blends and the microalgae biomass alone were placed in serum vials open to the atmosphere without acidification. Each experimental condition was performed in triplicate and each vial was stored in a dark environment to prevent continued photosynthesis. The storage experiments were conducted for 30 days in sealed vials purged at the beginning of the experiment with nitrogen gas.

FIGS. 1-4 show the morphologies of the biomass samples after 30 days storage. Under the anaerobic, acidified conditions, the microalgae biomass alone (FIG. 1) and the microalgae biomass blend (FIG. 2) were observed with good stability and material preservation. In comparison, the non-acidified aerobic controls exhibited heavy mold (microalgae biomass only, FIG. 3) or filamentous growth (microalgae biomass blend, FIG. 4), indicating significant deterioration of the microalgae biomass or the microalgae biomass blend.

Experiments to evaluate natural ensiling were conducted in 125 mL jars (Thermo Scientific, Waltham, MA) outfitted with an S-type fermentation airlock that enabled fermentation gases to escape while isolating the contents of the jar from atmospheric oxygen. The fermentation airlock was affixed to the jar lid through the use of a silicon grommet (9.5 mm ID, 14.3 mm OD). Fermentation gases were collected in TEDLAR® bags (P/N #GSTP000-0606, Jensen Inert Products, Coral Springs, FL) connected to the outlet of the fermentation airlock for quantitation and compositional analysis.

To encourage ensiling, an inoculum of *Lactobacillus acidophilus* was added at a loading of 100,000 cfu per g of wet biomass. Once blended, the biomass was compacted into pre-weighed jars up to the top to limit headspace; approximately 32 g dry material equivalent was added to each jar. The jars with biomass were weighed and immediately sealed with the lid/fermentation airlock assembly. Water was added to the fermentation airlock and the TEDLAR® bag was attached to complete the seal. The storage reactors were stored at room temperature in the dark. The experiment was performed in quadruplicate. Moisture content of fresh and stored materials was determined gravimetrically after drying at 105° C. until reaching a constant weight. Dry matter loss for each experiment was determined based on the dry matter entering and leaving the storage reactor. Data from the LAB inoculated samples is indicated in the figures by the term "natural ensiling."

The dry matter loss, initial pH and finial pH for the biomass samples are shown in Table 1. The microalgae biomass samples, both anaerobic and aerobic controls, where pH was not adjusted, exhibited high dry matter loss (43.9% and 36.8%, db, respectively). All acidified microalgae samples, in contrast, were better preserved, experiencing dry matter losses of 6.8% db to 14.2% db, at least a 67% reduction compared to the controls. It should be noted that the 36.8% dry matter loss of the aerobic stored microalgae biomass included the dry mass of mold that had grown on the samples and may not reflect the real loss of the initial material, which could be much higher. The microalgae biomass samples treated with a mixture of acetic and lactic acids experienced the lowest dry matter loss (6.8% db to 8.8%, db), which was much lower than dry matter losses observed for the lactic acid treated microalgae biomass samples or the microalgae biomass samples treated with sulfuric acid (12% db-14% db), suggesting that the combination of lactic and acetic acid act to preserve the microalgae biomass in ways beyond a simple reduction in pH. The inhibitory effects imparted by mixtures of lactic and acetic acids may have added benefits to stability should the microalgae biomass or microalgae biomass blend become exposed to oxygen and when the microalgae biomass or microalgae biomass blend is reclaimed for conversion. The benefits of heterolactic fermentation come at a cost of higher dry matter loss compared to homolactic fermentation, as 1 mole of carbon dioxide is produced for each mole of lactic and acetic acid. In addition, a combination of lactic and acetic acid may have a negative impact on biochemical conversion of the stored biomass to fuel by inhibiting the microorganism responsible for conversion. This potential limitation may be overcome by carefully selecting a silage inoculant that is compatible with the intended conversion technology.

degradation activity from the microalgae biomass blends and corn stover alone samples. In general, under anaerobic conditions, when the pH drops and reaches about 3 or 4, the metabolic activity, e.g., microbial activity, is highly inhibited.

TABLE 1

Dry matter losses and pH changes of biomass samples stored anaerobically for 30 days. Samples included corn stover, fresh microalgae, and microalgae/corn stover blends treated with various acids to simulate conditions of ensiling or controls of the same material stored directly without treatment.

| Storage Conditions | Dry matter loss (%)[a] | | | Corn Stover | | Microalgae | | Microalgae/Corn Stover blend | |
|---|---|---|---|---|---|---|---|---|---|
| | Corn stover | Algae | Algae/Corn stover | Initial pH | Final pH | Initial pH | Final pH | Initial pH | Final pH |
| 3% lactic acid | 3.9 (5.4)[b] | 12.4 (4.0) | 1.7 (0.79) | 4.02 | 4.11 | 3.97 | 4.25 | 4.52 | 4.44 |
| 5% lactic acid | 4.4 (0.04)[b] | 14.2 (4.8)[b] | negligible | 3.78 | 3.79 | 3.70 | 4.36 | 4.14 | 4.09 |
| 1% acetic, 3% lactic acid | negligible | 8.8 (0.80)[b] | 0.6 (0.22) | 4.03 | 4.61 | 3.69 | 4.38 | 4.19 | 4.40 |
| 2% acetic, 6% lactic acid | 3.7 (0.67) | 6.8 (0.93) | negligible | 3.76 | 4.21 | 3.38 | 4.30 | 3.66 | 3.80 |
| Sulfuric acid, pH ~4 | 1.0 (0.68) | 13.9 (1.3)[c] | 1.8 (0.78) | 4.10 | 4.81 | 3.86 | 4.52 | 3.96 | 4.31 |
| Sulfuric acid, pH ~2 | 3.6 (0.79) | 11.9 (6.4)[c] | 0.9 (0.73)[b] | 2.32 | 2.76 | 2.34 | 4.08 | 2.46 | 2.93 |
| Anaerobic control | 3.4 (2.8) | 43.9 (0.79) | 7.0 (0.43) | 7.57 | 4.94 | 6.24 | 7.31 | 6.43 | 4.94 |
| Aerobic control[d] | 5.0 (0.52) | 36.8 (4.3) | 21.4 (0.36) | 7.57 | 4.11 | 6.24 | 4.25 | 6.43 | 4.44 |
| Natural ensiling, 100 mL | NA | NA | 8.4 (1.6) | NA | NA | NA | NA | ND | 4.76 |

[a]Represents the average of triplicate experiments, standard deviation of the mean is listed in parenthesis.
[b]Average of two replicates, third replicate was judged a statistical outlier.
[c]Average of two replicates.
[d]Anaerobic and aerobic control experiments were initiated using the same biomass, as a result initial pH measurements are identical.
NA refers to measurements that are not applicable to a particular experiment. ND refers to a measurement that was not determined.

Under aerobic conditions, both the microalgae biomass blends and the corn stover alone had the highest dry matter loss (21.4% and 5.0%) compared to the same materials stored anaerobically (7.0% and 3.4%, respectively), indicating anaerobic storage is a better approach for preservation for the microalgae biomass. The anaerobic control of the microalgae/corn stover blend had a surprisingly low dry matter loss of 7.0% (compared to 43.9% for algae alone stored anaerobically), likely caused by microbial conversion of corn stover soluble sugars to organic acids, dropping the pH from 6.43 to 4.94 to stabilize the biomass. The acidified microalgae/corn stover blends treated with organic acids and sulfuric acids all exhibited dry matter losses lower than 2%. These results further confirm that anaerobic, low pH storage is a promising approach to stabilize microalgae biomass.

Although dry matter loss for corn stover controls, anaerobic- and aerobically stored, were generally low (3.4% and 5.0%, respectively), due to their inherent recalcitrant characteristics, acidification resulted in either similar or reduced dry matter loss (e.g., sulfuric acid pH ~4 and 1% acetic acid, 3% lactic acid). Increases of pH in sulfuric acid and acetic/lactic acid treated microalgae biomass blends and corn stover samples were observed after 30 days storage; however, there were no pH changes in the lactic acid treated microalgae biomass blends and corn stover. For all the acidified, stored microalgae samples, there were obvious pH increases, suggesting different microbial community and The proof-of-principle studies demonstrated the effectiveness of low pH and anaerobic conditions to stabilize microalgae biomass blends of microalgae and corn stover. The anaerobic microalgae/corn stover blend achieved surprisingly low dry matter loss when compared with the microalgae only anaerobic control, indicating the potential for microalgae/corn stover blends to naturally ensile.

To be economically viable at commercial scale, microalgae/corn stover blends will need to naturally ensile, producing organic acids needed for preservation in situ. A natural ensiling experiment (6× initial studies) was conducted to evaluate the storage performance of a microalgae/corn stover blend (20% microalgae, db) inoculated with *Lactobacillus acidophilus* at a rate consistent with forage ensiling to encourage growth of lactic acid bacteria and ensiling. By the end of the 35 day storage period the microalgae/corn stover biomass had lost 8.4% of its initial dry weight and the pH had been reduced below 4.76 (see Table 1), an outcome that is similar to the proof-of-principle anaerobic control. The dry matter loss and final pH were higher for the naturally ensiled sample than observed for the acidified microalgae biomass blends, indicating that more optimization needs to occur to promote greater production of endogenous organic acids. However, losses were within the range of the proof-of-principle anaerobic control and were significantly reduced compared to the aerobic control, indicating that natural ensiling of microalgae and corn stover blends is possible, yet more optimization needs to occur to produce sufficient levels of endogenous acid for preservation.

Example 5

Analysis of Fermentation Gases

The composition of fermentation gases produced during the storage experiments was determined by gas chromatography using a gas chromatograph (MicroGC 3000, Agilent, Santa Clara, CA) equipped with two Molecular Sieve 5 Å columns (10 m length×320 μm ID×12 μm film), one to quantify hydrogen and oxygen (argon carrier gas, 25 psi) and the other to measure methane and carbon monoxide (helium carrier gas, 25 psi) and a Plot U column (6 m length×320 μm ID×30 μm film) (helium carrier gas, 25 psi) to facilitate carbon dioxide measurement. Each column was connected to a thermal conductivity detector, which was calibrated using mixtures of relevant gases. During analysis, the temperature of the column and injector were both held at 60° C. For analysis, a sample of biogas was removed periodically from each serum vial using a gas-tight syringe.

Organic acids present in both fresh and stored biomass samples were extracted using a 1:10 ratio of wet biomass (1 g) to deionized water. The biomass samples were vortexed and equilibrated overnight, and then an aliquot was removed and filtered through a 0.2 μm syringe filter and acidified with 0.1 volume of 4 N $H_2SO_4$. Each extract was analyzed in duplicate using high-performance liquid chromatography (HPLC) with a refractive index detector (1200 series, Agilent, Santa Clara, CA). Individual organic acids were separated using an AMINEX® HPX 87H ion exclusion column (P/N 125-0140, Bio-Rad, Hercules, CA).

Figure 5:
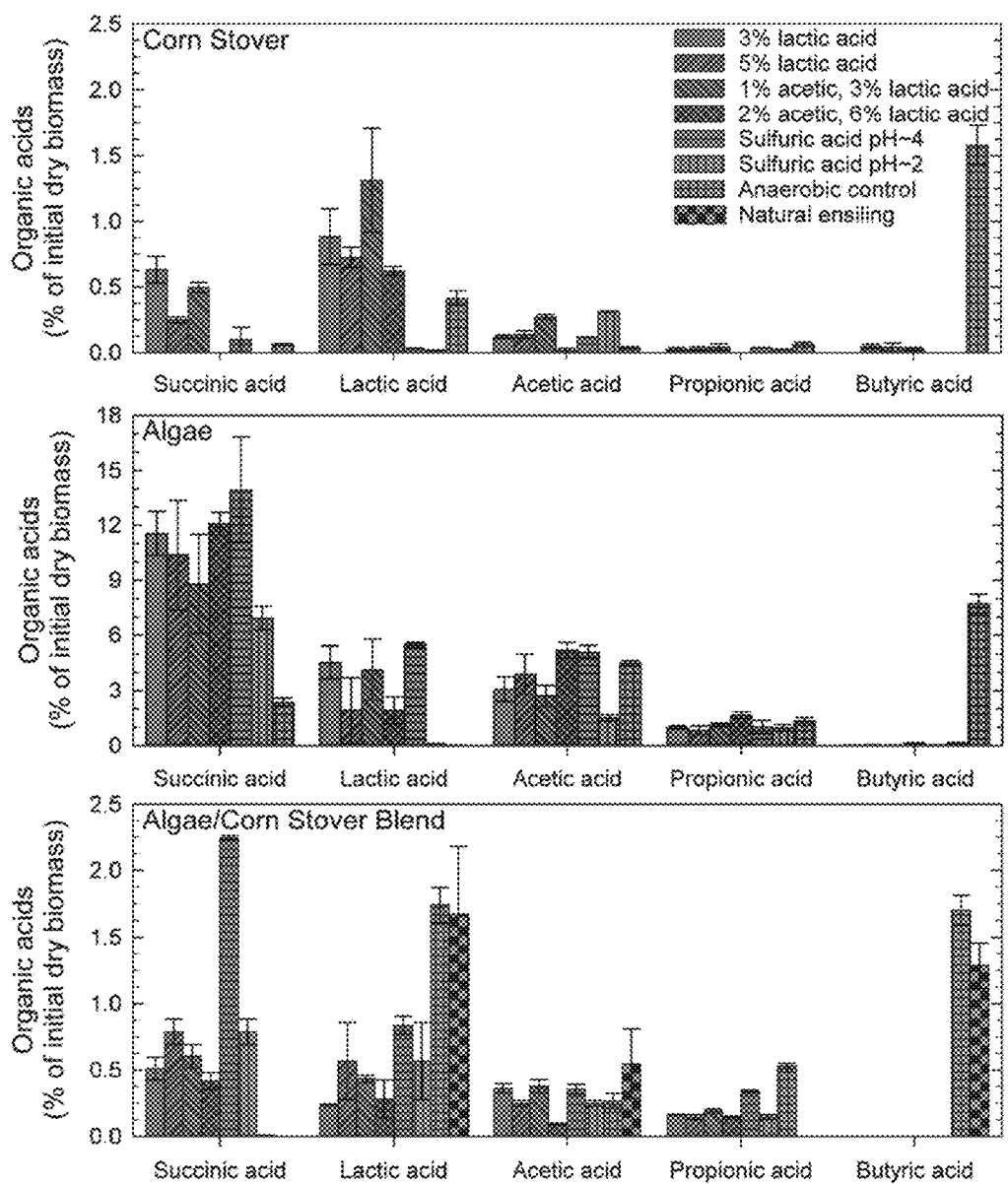
FIG. 5 includes bar graphs showing the production of organic acids from microalgae biomass, microalgae biomass blends, and herbaceous biomass treated with various acids according to embodiments of the disclosure.

During anaerobic wet storage, fermentative bacteria convert the carbohydrates, proteins, and lipids into volatile fatty acids, such as acetate, propionate, lactate, and butyrate, which facilitate the preservation of the biomass. Lower pH (~4) serves to inhibit the growth of microorganisms responsible for excessive degradation, including yeast, mold, and bacteria (e.g., *Clostridium* sp.) Additional acid production was not expected as none of the treatments were inoculated with lactic acid producing bacteria (e.g., *Lactobacillus*). After 30 days of storage, each biomass sample had more organic acids than initially measured, as shown in FIG. 5. Lactic acid was the primary organic acid produced in the acidified corn stover samples, while succinic acid and acetic acid were produced to a much lesser extent. In the anaerobic corn stover control, butyric acid was the primary fermentation product. This outcome was also observed for the anaerobic control for the microalgae/corn stover blends and the natural ensiling experiment (inoculating the microalgae/corn stover blends with LAB). Butyric acid is an indicator of Clostridia fermentation and is commonly associated with poorly ensiled material. *Clostridium* sp. consume either soluble sugars or lactic acid to produce butyric acid, hydrogen gas, and carbon dioxide, which leads to high dry matter loss and increased pH. The end application of most ensiled material is for livestock feed, where high butyric acid content reduces feed quality by lowering palatability and decreasing the nutritive value. Beyond higher dry matter loss, the impact of butyric acid fermentation on fuel yield is uncertain. Of the stored corn stover samples, the anaerobic control had the highest initial and final pH. Although real-time pH and organic acid concentrations were not measured, how quickly the pH of a sample is lowered may have an impact on the production of butyric acid by organisms, such as *Clostridium* sp.

Microalgae-only samples yielded significantly more organic acids than the microalgae/corn stover blends and neat corn stover samples. Particularly, high concentrations of succinic acid, up to 14% on a dry weight basis, were observed from all the microalgae samples. The highest succinic acid production was from the stored microalgae sample treated with a mixture of 2% acetic and 6% lactic acid, resulting in a yield of 0.34 g/g sugar, 25.6% of theoretical glucose conversion to succinic acid (1.33 g/g glucose), assuming total fermentable sugars in algae is 38% dry weight basis. Considering the high global market demand of succinic acid as a valuable bioproduct and intermediate, the conversion of the microalgae biomass during anaerobic storage deserves further investigation. The microalgae/corn stover blends also experienced increased succinic acid production relative to the stored corn stover. The microalgae/corn stover blends treated with sulfuric acid to achieve a pH of ~4 had the highest succinic acid yield, >2% of biomass (db).

Gas evolution often accompanies organic acid production and consists mostly of carbon dioxide with some observed hydrogen. The carbon dioxide and hydrogen production calculated on the basis of dry biomass for each material and experimental treatment is listed in Table 2. Consistent with the high level of degradation, the microalgae anaerobic control without pH adjustment had the highest observed carbon dioxide production (49.88 ml carbon dioxide/g dry biomass) over 30 days storage. In contrast, each acidified microalgae sample had little (<5 ml/g dry biomass) carbon dioxide production, the lone exception being the sulfuric acid treated sample (pH 4), where a carbon dioxide yield of 9.43 ml/g dry biomass was observed. The carbon dioxide produced from anaerobic controls of the microalgae/corn stover blends and corn stover alone samples was 8.88 and 2.47 ml/g dry biomass, respectively, much lower than the microalgae stored alone. This further demonstrates the benefit to stabilization that blending the microalgae biomass with terrestrial biomass, such as corn stover biomass, had and the potential of this strategy to preserve microalgal biomass quantity and quality.

TABLE 2

Carbon dioxide and hydrogen production for corn stover biomass alone, microalgae biomass alone, and microalgae/corn stover biomass blends.

| Storage Conditions | $CO_2$ Production (mL/g biomass) | | | $H_2$ Production (mL/g biomass) | | |
| --- | --- | --- | --- | --- | --- | --- |
| | Corn stover | Algae | Algae/Corn stover | Corn stover | Algae | Algae/Corn stover |
| 3% lactic acid | 1.32 (0.02) | 4.41 (2.61) | 0.32 (0.20) | 0 | 0 | 0 |
| 5% lactic acid | 0.16 (0.03) | 3.38 (3.23) | 0.15 (0.01) | 0 | 0 | 0 |
| 1% acetic, 3% lactic acid | 0.09 (0.02) | 1.81 (0.27) | 0.15 (0.00) | 0 | 0 | 0 |

TABLE 2-continued

Carbon dioxide and hydrogen production for corn stover biomass alone,
microalgae biomass alone, and microalgae/corn stover biomass blends.

| Storage Conditions | $CO_2$ Production (mL/g biomass) | | | $H_2$ Production (mL/g biomass) | | |
|---|---|---|---|---|---|---|
| | Corn stover | Algae | Algae/Corn stover | Corn stover | Algae | Algae/Corn stover |
| 2% acetic, 6% lactic acid | 0.07 (0.00) | 1.42 (0.12) | 0.14 (0.00) | 0 | 0 | 0 |
| Sulfuric acid, pH ~4 | ND | 9.43 (5.45) | 0.64 (0.06) | ND | 0.21 (0.25) | 0 |
| Sulfuric acid, pH ~2 | 0.10 (0.01) | 0.52 (0.30) | 0.31 (0.10) | 0 | 0.01 (0.01) | 0 |
| Anaerobic control | 2.47 (0.24) | 49.87 (2.57) | 8.88 (2.44) | 1.08 (0.06) | 5.35 (0.73) | 1.72 (0.43) |
| Natural ensiling, 100 mL | NA | NA | 8.75 (10.27) | NA | NA | 0 |

[a]Cumulative gas production (mL/g biomass) monitored over a 30 day period.
Numbers listed in parenthesis represent standard deviation of the mean.

The composition of gas generated throughout storage primarily included carbon dioxide, although hydrogen was produced in the anaerobic control of each material, reaching 5.4 ml/g biomass in the microalgae only samples and 1.7 ml/g biomass and 1.1 ml/g biomass of the microalgae biomass blend and corn stover only, respectively. No methane production was observed in any of the experiments, indicating low methanogen activity under the acidic, anaerobic environment. Certain species of microalgae, including *Scenedesmus obliquus* used in the current study, contain genes encoding the protein responsible for hydrogen production (hydrogenase), which is expressed under hypoxic conditions independent of illumination. In addition, microalgal biomass has been reported as an interesting alternative substrate for hydrogen production by *Clostridium* sp., which could be inadvertently introduced into the storage system from the environment. *Clostridium* sp. commonly are introduced to herbaceous silage piles through harvesting operations that entrain dirt. Once incorporated into a storage pile, *Clostridium* sp. can flourish, as they are well known to utilize soluble sugars and structural carbohydrates in the biomass to produce hydrogen, organic acids, and alcohols.

Example 6

Biomass Compositional Changes as a Result of Storage

Unstored and stored microalgae/corn stover blends and corn stover alone samples were ground with a Retsch ZM 200 Ultra Centrifugal Mill (Retsch, Haan, Germany) to pass through a 0.2-mm screen and homogenized prior to conducting proximate and ultimate analyses. For proximate analysis (i.e., moisture, volatile, ash, and fixed carbon content), a LECO TGA701 Thermogravimetric Analyzer (St. Joseph, MI) following ASTM D 5142-09 was used (ASTM International, West Conshohocken, PA). Briefly, the biomass samples were heated to and maintained at 107° C. until a constant mass was reached under a 10 L/minute nitrogen flow to measure the moisture content. The temperature was then ramped to 950° C. and held for 7 minutes to determine volatiles. After cooling to 600° C., ash content was determined by switching the gas flow to 3.5 L/minute of oxygen and increasing the temperature to 750° C. until a constant mass was reached. Fixed carbon was determined by the weight loss between the volatile and ash measurements. Ultimate analysis, determining elemental C, H, N, and S concentrations, was performed using a LECO TRUSPEC® CHN with S add-on module (St. Joseph, MI) following ASTM D5373-10 [27, 28] and ASTM D4239-10 [27] (ASTM International, West Conshohocken, PA), respectively. Oxygen was determined by difference. The biomass samples were run in triplicate for proximate, elemental CHN, and elemental S analyses.

Proximate and ultimate analysis was conducted on each of the treated microalgae/corn stover blends before and after 30 days storage to better understand how storage conditions affect the biomass composition. As shown in Tables 3 and 4, the proximate analysis and ultimate analysis revealed that volatile matter decreased significantly as a result of storage in the lactic acid treated samples, low concentration lactic and acetic acid treated samples, sulfuric acid treated samples, and aerobic control samples. Reduced volatile matter is generally associated with decreased acidity, which will reduce corrosion during in conversion, and with increased energy density. The percentage of fixed and total carbon within the microalgae/corn stover blends was affected in some cases by storage. Fixed carbon increased significantly in all but one of the lactic and acetic/lactic acid treated samples. Aerobic storage resulted in a significant decrease in total carbon content of the microalgae/corn stover blends, as well as an increase in ash content, consistent with the large dry matter loss observed in this biomass during aerobic storage. Wet anaerobic storage of the microalgae/corn stover blends treated with either lactic acid or a mixture of acetic and lactic acids significantly enriched total carbon. The carbon to oxygen (C:O) ratio and carbon to hydrogen (C:H) ratio either increased (organic acids, sulfuric acid pH 4) or remained unchanged (C:O ratio, sulfuric acid pH 2) as a result of storage when treated with acid, while untreated samples experienced a decrease. Higher C:O and C:H ratios result in higher energy densities and thus higher conversion efficiency.

TABLE 3

Proximate analysis of microalgae/corn stover blends before storage and after 30 days storage.

| Treatment | Volatiles (wt %) Before[a] | Volatiles (wt %) After[b] | Fixed Carbon (wt %) Before | Fixed Carbon (wt %) After | Ash (wt %) Before | Ash (wt %) After |
|---|---|---|---|---|---|---|
| 3% Lactic acid | 80.42* (0.55) | 79.20 (0.26) | 14.02 (0.54) | 15.21* (0.25) | 5.06 (0.02) | 5.07 (0.02) |
| 5% Lactic acid | 80.75* (0.58) | 79.47 (0.45) | 14.02 (0.60) | 15.21 (0.44) | 5.23 (0.02) | 5.33 (0.01) |
| 1% acetic acid, 3% lactic acid | 80.72* (0.50) | 79.74 (0.09) | 14.58 (0.48) | 15.65* (0.07) | 4.70 (0.02) | 4.61 (0.03) |
| 2% acetic acid, 6% lactic acid | 80.03 (0.17) | 79.79 (0.18) | 15.28 (0.16) | 15.28* (0.19) | 4.69 (0.03) | 4.90 (0.02) |
| Sulfuric acid pH 4 | 80.70* (0.34) | 79.32 (0.75) | 13.55 (0.36) | 14.91 (0.77) | 5.75 (0.02) | 5.77 (0.09) |
| Sulfuric acid pH 2 | 77.87 (0.39) | 78.83 (0.68) | 16.18 (0.35) | 15.84 (0.68) | 5.94 (0.08) | 5.83 (0.08) |
| Aerobic control[c] | 79.67* (0.17) | 78.00 (0.30) | 15.60 (0.18) | 16.08 (0.29) | 4.73 (0.01) | 5.92 (0.02) |
| Anaerobic control[c] | 79.67 (0.17) | 79.89 (0.37) | 15.60 (0.18) | 14.94 (0.39) | 4.73 (0.01) | 5.17 (0.02) |

[a]Proximate and ultimate data collected from pre-storage material.
[b]Proximate and ultimate analysis conducted on material after 30 days of storage for each storage condition.
[c]Both the aerobic control and anaerobic control utilized the same material. As a consequence, the post-storage proximate and ultimate analysis for each control are compared to proximate and ultimate analysis of the same pre-storage material.
*Denotes measurements determined to be significant by one way, single factor ANOVA analysis.
Numbers listed in parenthesis represent the standard deviation.

TABLE 4

Ultimate analysis of microalgae/corn stover blends before storage and after 30-day storage.

| Treatment | Carbon (wt %) Before | Carbon (wt %) After | Hydrogen (wt %) Before | Hydrogen (wt %) After | Nitrogen (wt %) Before |
|---|---|---|---|---|---|
| 3% Lactic acid | 47.66 (0.02) | 48.02* (0.01) | 5.98 (0.10) | 5.91 (0.01) | 1.78 (0.02) |
| 5% Lactic acid | 47.45 (0.09) | 47.83* (0.04) | 5.98 (0.01) | 5.92 (0.01) | 1.75 (0.02) |
| 1% acetic acid, 3% lactic acid | 47.60 (0.08) | 48.19* (0.05) | 6.02 (0.01) | 5.91 (0.03) | 1.74 (0.01) |
| 2% acetic acid, 6% lactic acid | 47.56 (0.02) | 48.07* (0.04) | 6.00 (0.02) | 5.95 (0.01) | 1.64 (0.01) |
| Sulfuric acid pH 4 | 47.29 (0.20) | 47.51 (0.10) | 5.96 (0.07) | 5.86 (0.03) | 1.72 (0.02) |
| Sulfuric acid pH 2 | 46.66 (0.03) | 46.74 (0.10) | 5.93 (0.0) | 5.82 (0.01) | 1.79 (0.01) |
| Aerobic control[c] | 47.89* (0.02) | 47.40 (0.05) | 5.93 (0.06) | 5.85 (0.02) | 1.71 (0.03) |
| Anaerobic control[c] | 47.89 (0.02) | 47.85 (0.03) | 5.93 (0.06) | 5.98 (0.0) | 1.71 (0.03) |

| Treatment | Nitrogen (wt %) After | Oxygen (wt %) Before | Oxygen (wt %) After | C:O Ratio Before | C:O Ratio After | C:H Ratio Before | C:H Ratio After |
|---|---|---|---|---|---|---|---|
| 3% Lactic acid | 1.84* (0.01) | 39.34 (0.10) | 38.96 (0.03) | 1.21 | 1.23 | 7.97 | 8.13 |
| 5% Lactic acid | 1.85* (0.0) | 39.42 (0.11) | 38.88 (0.04) | 1.20 | 1.23 | 7.93 | 8.08 |
| 1% acetic acid, 3% lactic acid | 1.78* (0.01) | 39.76 (0.08) | 39.32 (0.08) | 1.20 | 1.23 | 7.91 | 8.15 |
| 2% acetic acid, 6% lactic acid | 1.83* (0.01) | 39.96 (0.19) | 39.04 (0.02) | 1.19 | 1.23 | 7.93 | 8.08 |
| Sulfuric acid pH 4 | 1.83* (0.01) | 38.72 (0.13) | 38.45 (0..01) | 1.22 | 1.24 | 7.93 | 8.11 |
| Sulfuric acid pH 2 | 1.76 (0.03) | 38.69 (0.01) | 38.79 (0.12) | 1.21 | 1.20 | 7.87 | 8.03 |
| Aerobic control[c] | 2.20* (0.01) | 38.56 (0.06) | 38.40 (0.08) | 1.24 | 1.23 | 8.08 | 8.10 |

TABLE 4-continued

Ultimate analysis of microalgae/corn stover blends before storage and after 30-day storage.

| Anaerobic control[c] | 1.81* (0.01) | 38.56 (0.06) | 39.00 (0.03) | 1.24 | 1.23 | 8.08 | 8.00 |

[a]Proximate and ultimate data collected from pre-storage material.
[b]Proximate and ultimate analysis conducted on material after 30 days of storage for each storage condition.
[c]Both the aerobic control and anaerobic control utilized the same material. As a consequence, the post-storage proximate and ultimate analysis for each control are compared to proximate and ultimate analysis of the same pre-storage material.
*Denotes measurements determined to be significant by one way, single factor ANOVA analysis.
Numbers listed in parenthesis represent the standard deviation.

Nitrogen was significantly enriched as a result of storage with the exception of the sulfuric acid pH 2 sample. The relatively high concentration of nitrogen in the biomass is a concern for thermochemical conversion, where nitrogen reduces the quality of oil produced and necessitates additional processing steps to remove it. No significant difference in sulfur content was observed as a result of storage. The sulfur content was elevated in storage treatments which were treated with sulfuric acid, relative to other treatments and controls. Sulfuric acid treatments may be less desirable for thermochemical approaches to fuel conversion, such as hydrothermal liquefaction, due to potential sulfur emissions but may be beneficial to biochemical conversion strategies that rely on dilute acid pretreatment with sulfuric acid in order to make sugars more accessible for conversion. Storage did not appear to significantly affect the hydrogen or oxygen content.

Example 7

$N_2$ or $CO_2$ Purge Experiments

Figure 6:
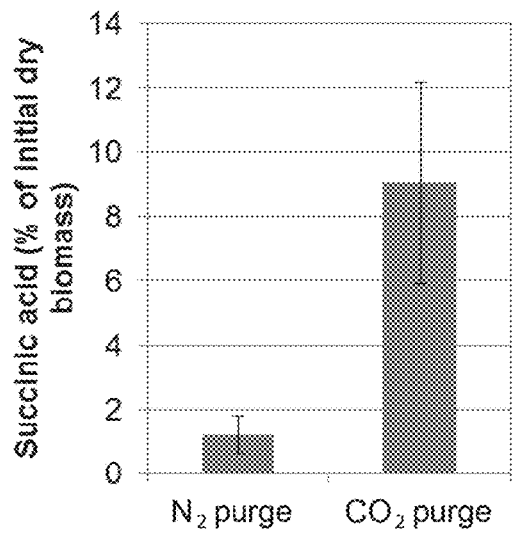
FIG. 6 is a bar graph showing the production of succinic acid from acid-treated microalgae biomass samples and purged with nitrogen ($N_2$) or carbon dioxide ($CO_2$) according to embodiments of the disclosure.

Acidified microalgae biomass samples were purged with nitrogen gas ($N_2$) or carbon dioxide ($CO_2$) gas. The microalgae biomass was produced as described above in Example 1 and was acidified with 0.5% by weight sulfuric acid followed by either a single $N_2$ purge or a single $CO_2$ purge prior to the 30 day storage period. As shown in FIG. 6, the microalgae biomass sample purged with $CO_2$ produced significantly more succinic acid than the sample purged with $N_2$. About 9% succinic acid was produced following the $CO_2$ purge, compared to about 1% succinic acid following the $N_2$ purge.

Example 8

Succinic Acid Production

Figure 7:
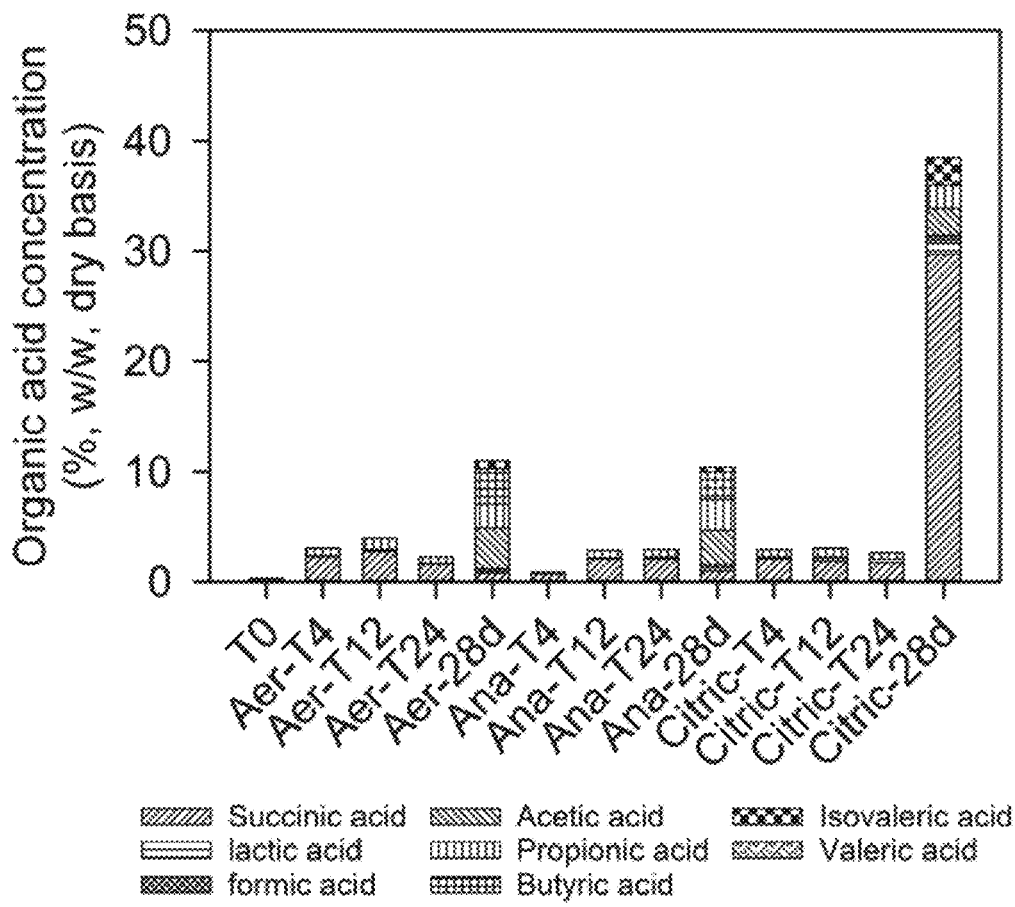
FIGS. 7 and 8 are bar graphs showing the production of organic acids from citric acid-treated microalgae biomass samples.

The effect of citric acid addition on succinic acid production was investigated. Citric acid was added to samples of *Scenedesmus obliquus* biomass obtained as described above in Example 1. The citric acid was added to the samples at about 5% db. Control samples lacking citric acid (untreated samples) were also prepared. The samples were stored under ambient (Aer) and anaerobic (Ana) conditions. The coproduct organic acids were measured by conventional techniques at time points including 4 hours, 12 hours, 24 hours, and 28 days. The measured organic acids included succinic acid, lactic acid, formic acid, acetic acid, propionic acid, butyric acid, isovaleric acid, and valeric acid. The organic acid content for each sample at the indicated time point is shown in FIG. 7.

In the first 24 hours, there was little difference in the amount of organic acid produced or its composition between the citric acid treated samples and the untreated samples. However, after 28 days, there were large differences between the citric acid treated samples and the untreated samples. As shown in FIG. 7, the citric acid treated samples unexpectedly included organic acid concentrations that reached up to about 45% of the total biomass (dry basis), with greater than about 25% succinic acid db produced, such as greater than about 30% succinic acid db, greater than about 40% succinic acid db, or greater than about 43% succinic acid db. In comparison, the untreated samples included organic acid concentrations of about 10% of the total biomass db and the produced organic acids predominantly included acetic acid, propionic acid, and butyric acid. Therefore, succinic acid titers reached about 86 g/L in the stored microalgae samples, assuming algae biomass to have a density of 1 g/mL (wet basis). In comparison, laboratory titers achieved in *Actinobacillus succinogenes* cultivations were significantly lower, at about 53 g/L.

Figure 8:
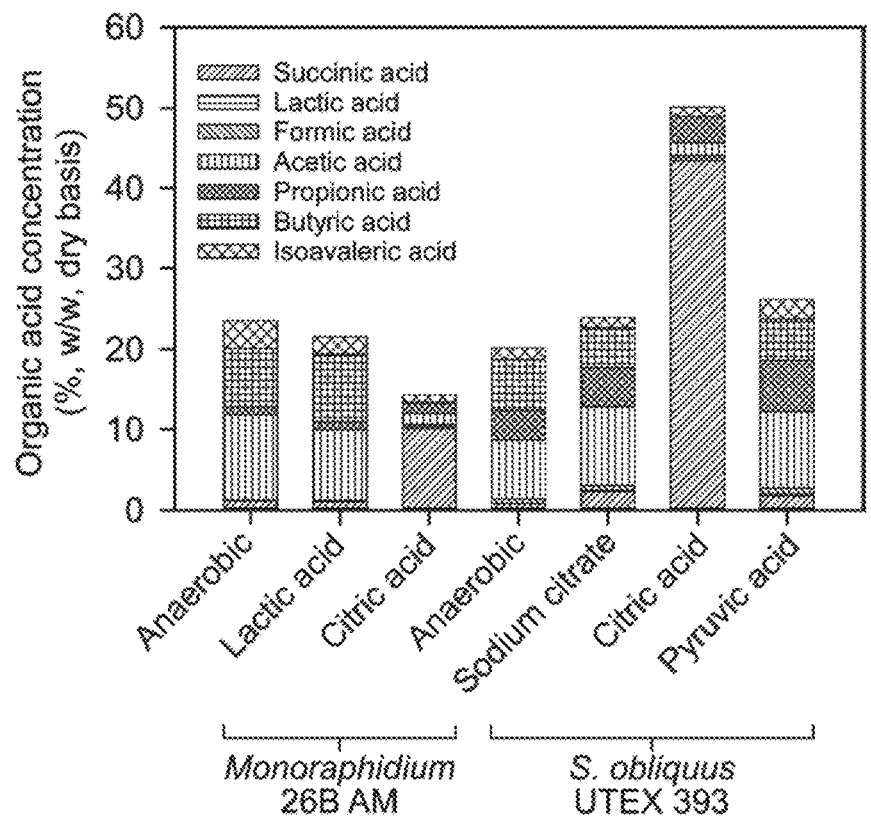

In additional samples, the citric acid was added to *Scenedesmus obliquus* samples at about 1% db. Additional organic acids (sodium citrate, pyruvic acid) were also tested in the *Scenedesmus obliquus* samples. Control samples (under anaerobic conditions) were tested along with the *Scenedesmus obliquus* samples. Samples in Monoraphidium were also prepared using lactic acid and citric acid, with control samples tested under anaerobic conditions. As shown in FIG. 8, the citric acid treated samples in the *Scenedesmus obliquus* biomass samples unexpectedly included organic acid concentrations that reached up to about 40% of the total biomass dry basis, with greater than about 40% succinic acid db produced.

Example 9

Succinic Acid Separation and Recovery

Figure 9:
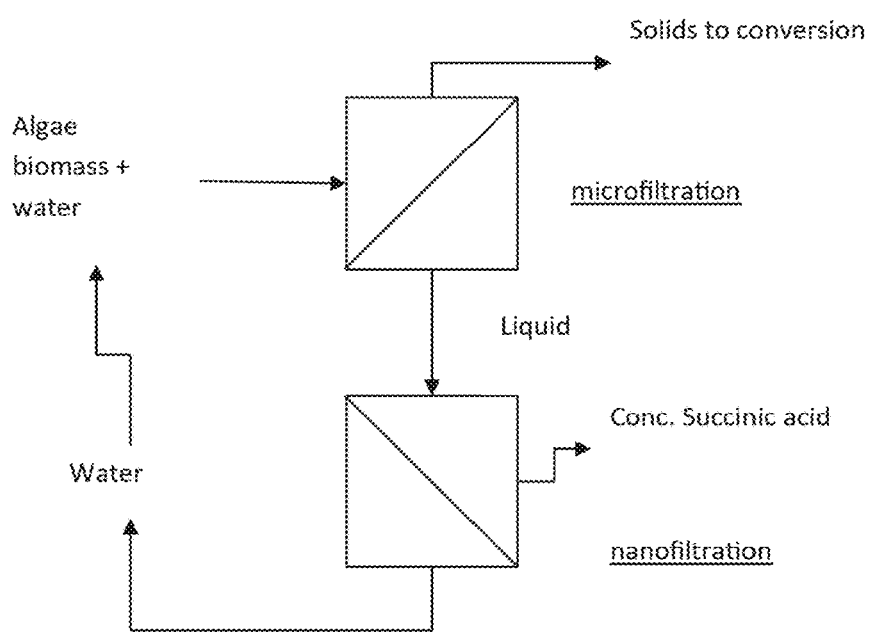
FIG. 9 is a schematic of a separation system used to recover organic acid coproducts by a separation process.

To recover succinic acid from the citric acid treated, *Scenedesmus obliquus* biomass samples, a separation process was conducted, as shown in FIG. 9. The citric acid treated biomass included succinic acid at about 0.3% by wet weight basis (about 5% on a dry weight basis) and trace amounts of other water-soluble organic acids. Water was added to the citric acid treated biomass to dilute the biomass and form a citric acid treated biomass solution that included the citric acid and other water-soluble components. The citric acid treated biomass was diluted 10 fold with water. The citric acid treated biomass solution was allowed to equilibrate for 24 hours, and subjected to a microfiltration process to remove solids from the citric acid treated biomass solution and produce a permeate containing the citric acid and other water-soluble components. A glass fiber microfiltration membrane having a 0.2 mm pore size was used to filter the citric acid treated biomass solution. The recovered solids were used in downstream conversion processes. The permeate from the microfiltration process was then filtered by a nanofiltration process using a DOW NF90 nanofiltration membrane having a molecular weight cutoff of about 90 amu. The nanofiltration membrane had an area of about 42 $cm^2$. Since the molecular weight of succinic acid is about 118 amu, concentrated succinic acid was recovered following the nanofiltration process. Water was recovered from the nanofiltration process for reuse in subsequent process stages.

Figures 10A, 10B:
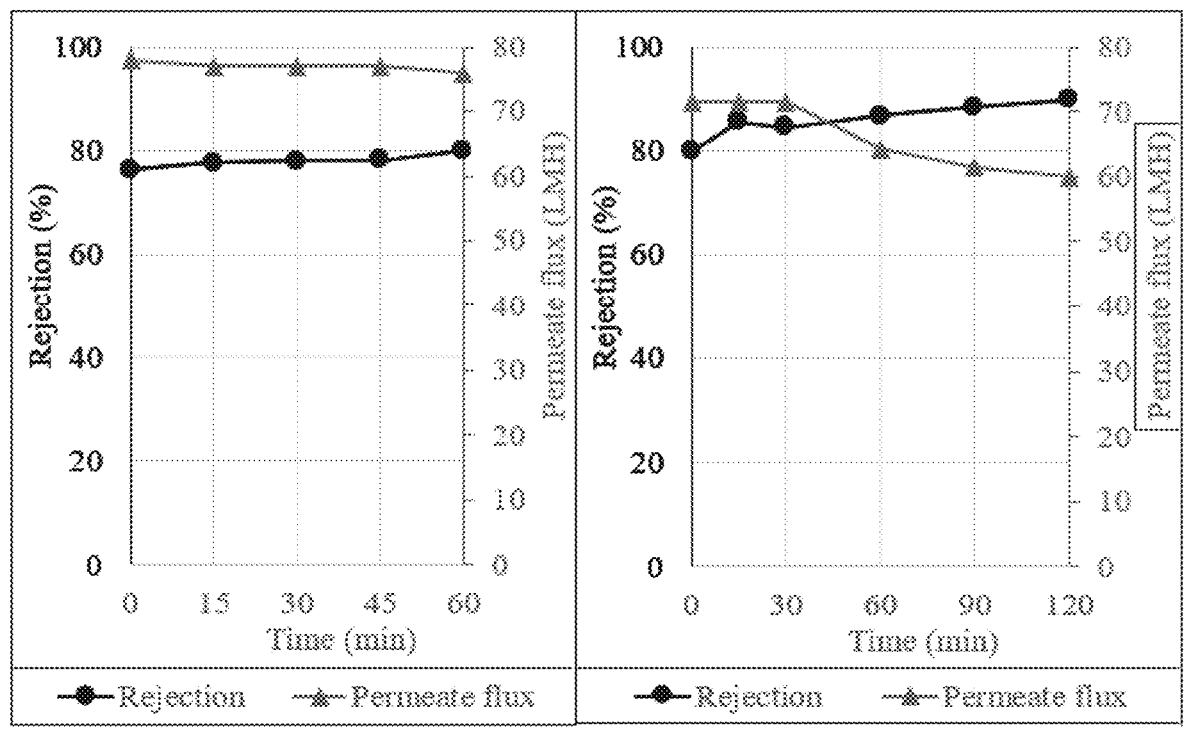
FIGS. 10a and 10b are graphs showing succinic acid rejection and permeate flux as a function of time.

The amount of succinic acid in the feed to the nanofiltration process and permeate was measured by conventional HPLC techniques. A one-hour long experiment was conducted at 50 psi transmembrane pressure on cross-flow mode with all of the permeate being recycled back to the microfiltration process. Permeate and feed samples were collected every fifteen minutes (steady-state, see FIG. 10a). The second experiment was a two-hour long experiment done at 50 psi transmembrane pressure on cross-flow mode, with the permeate being collected separately from the feed and, as a result, the feed volume continuously decreased (non-steady state, see FIG. 10b). The permeate and feed samples were collected every thirty minutes and HPLC analysis was conducted to quantify succinic acid in the feed and permeate fractions. As shown in FIG. 10a for the steady-state experiment, transmembrane flux remained steady for the duration of the experiment at about 78 LMH ($L_{permeate}$ $m^{-2}_{membrane}$ $hr^{-1}$) and succinic acid rejection was about 80%. As shown in FIG. 10b for the non-steady-state experiment, the succinic acid concentration in the feed increased since the permeate was not added back. As a result, the flux decreased from about 75 to about 60 LMH with the rejection going up from about 80% to about 90% during the non-steady-state experiment. Therefore, membrane separation was successful for recovery of the succinic acid from the citric acid treated biomass. A flux of 20 LMH or higher is considered sufficient flux for an industrial application, and this flux was maintained throughout concentration and succinic acid rejection remained high.

Example 10

Figure 11:
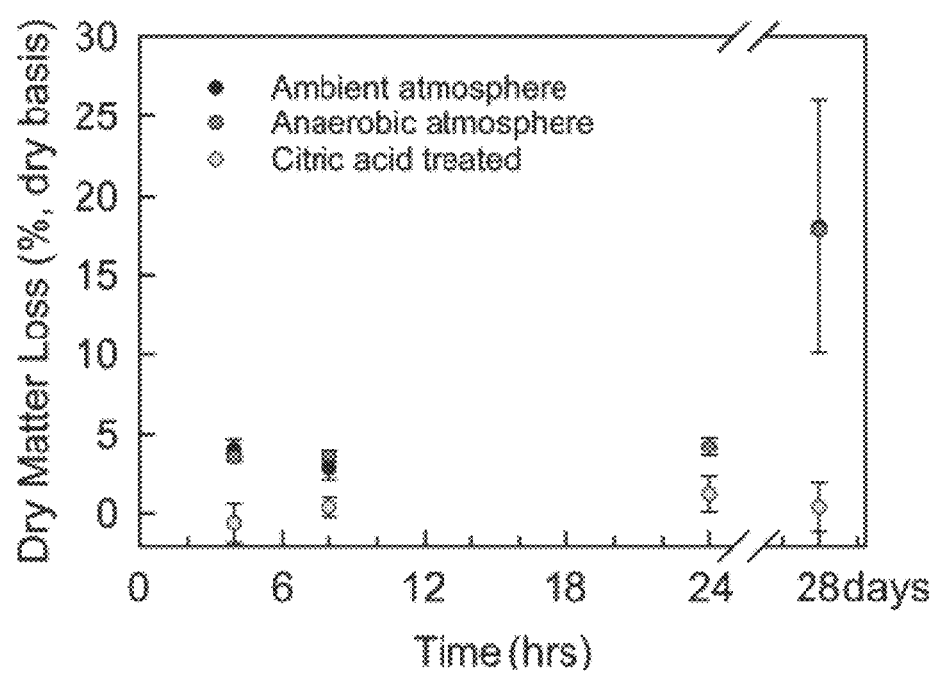
FIG. 11 is a graph showing dry matter loss occurring in storage of untreated and citric acid treated Tetradesmus obliquus UTEX 393 as a function of time.

Proteomic Analyses and Comparison of Untreated Biomass and Citric Acid Treated Biomass A storage experiment was conducted to evaluate storage losses within the first 24 hours of storage versus within the first month (28 days, 4 weeks). Storage for 4 weeks was chosen as the time frame to simulate a storage scenario where biomass was being preserved to mitigate seasonal variation. The biomass used was prepared similar to the biomass described in Examples 1 and 8. The treated biomass was exposed to 5% citric acid on a dry basis at room temperature. The storage experiments accounted for a 24-hour surge capacity to mitigate for variations in productivity and provide a constant flow of material to the conversion facility, where this variable length of time between harvest is known as conversion queuing. This experiment provided insight into losses that occur daily in queuing operations as algae productivities could exceed the immediate capacity to convert the biomass to fuels and chemicals, and the conversion of this material was delayed. It was found that untreated algae biomass was susceptible to degradation within queuing, losing 4% of algae biomass after 24 hours after harvest (FIG. 11). When the untreated biomass was stored for 28 days, 18% of total biomass was lost to degradation. When the algae biomass was treated with citric acid, losses were limited to 1% within the first 24 hours without further degradation observed over 28 days. Citric acid treatment also had the unexpected added benefit of accumulating succinic acid that amounted to 30% of the biomass based on dry weight, a co-product that could reduce the cost of algae biomass production.

As the algae were stored at the peak of their metabolic capacity, it was anticipated that the algae would continue to be metabolically active during storage, where the algal metabolic activity was proposed as a potential source of dry matter loss. Another potential source of dry matter loss was the microbial community accompanying the microalgae biomass. It was found that citric acid treatment supported the growth of bacteria associated with well-ensiled biomass, such as lactic acid bacteria (e.g., *Lactobacillus* sp.), and inhibited the growth of bacteria found in highly degraded biomass such as Clostridia. When biomass was stored without citric acid treatment, Clostridia was found in high abundance. It was hypothesized that the unexpected increase of Clostridia contributed significantly to the degradation observed in the untreated biomass ("anaerobic atmosphere" in FIG. 11). The contribution of microalgal metabolism was unknown.

Proteomic experiments were conducted comparing the relative abundance of proteins found in the initial biomass to biomass that had been stored for 24 hours and 28 days (4 weeks) without treatment and after treatment with citric acid to identify (1) how alterations to algae metabolism contributed to biomass preservation or degradation and (2) whether algae metabolism contributed to the accumulation of succinic acid as a byproduct of storage when treated with citric acid.

Algae-enriched and bacteria-enriched samples were prepared in house by extracting proteins that were then sent to a proteomics facility (Michigan State University) for digestion, derivatization and mass-spectral analysis. Data analysis was performed using MaxQuant (Max Planck Institute) software and a publicly available genomics database for UTEX 393. The data was then visualized, quantified and evaluated using Scaffold Viewer (Proteome Software, Inc.) software. Differences in each sample were evaluated on both macro and micro levels by looking at the sum of differences and differences in individual pathways. The macro analysis compared the number of proteins differentially expressed from the initial biomass for each treatment and time points (see Table 5). Differences were observed based on treatments and time as compared to the initial biomass as well as differences within treatments based on time. Samples were determined to be changed if their $Log_2Fold$ change was +/−1 compared to the initial conditions, indicating a change in protein expression level by either two-fold or half of the initial algae conditions.

TABLE 5

Total Protein Expression Changes Between Untreated and Citric Acid Treated Samples.

| | Storage Condition | Total Number of Proteins Changed | Number of Proteins Up-regulated | Number of Proteins Down-Regulated |
| --- | --- | --- | --- | --- |
| Citric Acid | 0 hr and 24 hr | 20 | 11 | 9 |
| | 0 hr and 28 days | 218 | 101 | 117 |
| | 24 hr and 28 days | 294 | 131 | 164 |
| Untreated | 0 hr and 24 hr | 137 | 69 | 68 |
| | 0 hr and 28 days | 924 | 589 | 335 |
| | 24 hr and 28 days | 961 | 364 | 597 |

The untreated biomass that did not preserve well showed a substantially higher change in protein expression levels than the citric acid-treated biomass, which were well-preserved biomass. After 24 hours, 137 proteins in the untreated samples exhibited a two-fold change in expression as a combination of increased and decreased expression. By sharp contrast, citric acid treated biomass exhibited a change in expression of only 20 proteins. Protein expression was found to have changed even more extensively after 28 days where 961 proteins, about ⅓ of the proteins identified, had changed. Between the initial starting conditions and the 28-day mark, 924 proteins showed a significant change in expression levels. Changes between time points were also evident as 964 proteins had altered expression from 24 hours to 28 days storage in the untreated biomass. After 28 days, a total of 218 proteins had changed in expression, indicating that citric acid treatment reduced losses in storage by limiting metabolic changes or created a cellular environment where cells are less able to modify their metabolism through pH changes or other effects.

Succinic Acid Accumulation

Citric acid treatment of algae biomass prior to storage increased its stability in long-term storage. UTEX 393 biomass accumulated succinic acid in concentrations in excess of 20% (dry basis, db) and up to 40% db of total biomass. Cross-referencing the proteomic data with known pathways of succinic acid accumulation (glyoxylate cycle, GABA shunt, reductive TCA cycle or TCA cycle) did not reveal a conclusive pathway that increased protein expression only in the presence of citric acid in UTEX 393 (Table 6).

TABLE 6

Alterations of protein expression levels for proteins involved in pathways involving succinic acid in untreated and citric acid treated biomass that were stored for 28 days.

| Protein | Pathway | Untreated (28 days) | Citric Acid (28 days) |
|---|---|---|---|
| Citrate synthase | TCA cycle | 1.98*** | 1.47 |
| | | 1.54*** | 1.14 |
| Aconitase | TCA cycle/Reductive TCA cycle | 1.18 | 1.02 |
| Isocitrate dehydrogenase | TCA cycle/Reductive TCA cycle | 1.27 | 1.96*** |
| | | 1.65*** | 1.07 |
| Alpha-ketoglutarate dehydrogenase | TCA cycle | 0.91 | 1.19 |
| Succinyl-coA synthetase | TCA cycle/Reductive TCA cycle | 2.23**** | 1.24 |
| Succinate dehydrogenase | TCA cycle | 1.50 | 1.31 |
| | | 1.87*** | 1.50 |
| Fumarase | TCA cycle | 1.04 | 1.53*** |
| ATP-citrate lyase | Reductive TCA cycle | 1.42 | 1.42 |
| | | 2.38**** | 1.94*** |
| Ferrodoxin | Reductive TCA cycle | 0.46* | 0.50* |
| | | 0.53** | 0.74** |
| | | 0.41* | 0.43* |
| Malate Dehydrogenase | TCA cycle/Reductive TCA cycle | 1.88*** | 2.05**** |
| | | 0.69** | 1.29 |
| | | 1.96*** | 1.35 |
| | | 1.77*** | 1.25 |
| Isocytrate lyase | Glyoxylate cycle | 1.81*** | 1.46 |
| Glutamate synthase | GABA Shunt | 2.07**** | 2.12**** |
| | | 0.77 | 0.93 |
| Pyruvate dehydrogenase | | 3.61**** | 1.40 |
| | | 2.53**** | 1.43 |
| | | 2.39**** | 1.16 |

The values marked with asterisks (*) indicate those proteins with either increased or decreased expression levels. Values marked with ** increased by a factor of 2 (i.e., doubled in expression), * increased by a factor of 1.5. For the proteins that decreased in expression, values marked with ** indicate those proteins that experienced at least a 30% decrease in expression (i.e., the proteins were expressed at most 0.7 that of the initial condition), and * indicates that the expression level was reduced by at least half (0.5).

Without being bound to any theory, it is believed that succinic acid accumulated in the citric acid treated algae biomass because its entry to other pathways was limited. In the untreated cells, intermediates that accumulated from amino acid degradation were "pulled" from the mitochondrial TCA pool through the actions of malate dehydrogenase (MDH) and phosphoenolpyruvate carboxykinase (PEPCK) and channeled to the products acetate and $CO_2$. The underlying mechanism of how citric acid exerts this control over MDH and PEPCK expression was unclear.

Example 11

Determining Changes in Amino Acid Distribution in Scenedesmus UTEX 393 Biomass in Storage that were Untreated and Treated with Citric Acid Measuring the total amino acid content along with free amino acid content provided greater insight into how protein content changed due to storage (Table 7). The total hydrolyzed amino acid test first hydrolyzed proteins to amino acids, which were then quantified. Each amino acid was summed to produce at the total protein content. The initial biomass had a protein content of 42% db. Citric acid treated biomass experienced an 8% reduction in protein content after 28 days. The greatest change in protein content occurred in the untreated sample after 28 days of anaerobic storage with 29% of the protein (db) being lost. Protein loss appeared to occur rapidly after harvest with 28% of the protein being lost after 24 hours. Protein loss was attributed to proteolysis of protein to generate free amino acids and subsequent fermentation of the free amino acids.

TABLE 7

Effect of treatment with citric acid and storage duration on amino acid composition of UTEX 393 algae biomass:

| | | Citric | | Untreated | |
|---|---|---|---|---|---|
| Amino acid | Initial Biomass gAA/kg algae | 24 hr gAA/kg initial algae* | 28 days gAA/kg initial algae* | 24 hr gAA/kg initial algae* | 28 days gAA/kg initial algae* |
| L-HydroxyProline | 0.00 | 0.00 | 0.00 | 0.00 | 0.00 |
| ASX | 40.4 | 39.0 | 37.9 | 28.3 | 24.2 |
| L-Threonine | 21.9 | 20.8 | 20.1 | 15.1 | 13.3 |
| L-Serine | 18.3 | 16.8 | 16.2 | 12.3 | 10.3 |
| GLX | 49.5 | 45.6 | 44.1 | 33.6 | 33.3 |
| L-Proline | 21.9 | 21.0 | 20.3 | 15.3 | 12.9 |
| L-Glycine | 23.5 | 23.0 | 22.4 | 16.7 | 18.8 |
| L-Alanine | 36.8 | 34.7 | 33.9 | 25.8 | 32.1 |
| L-Cysteine | 5.5 | 4.7 | 4.0 | 5.1 | 3.1 |
| L-Valine | 25.4 | 25.3 | 24.6 | 18.3 | 22.9 |
| L-Methionine | 11.0 | 9.6 | 8.6 | 10.5 | 8.5 |
| L-Isoleucine | 18.3 | 18.1 | 17.6 | 13.1 | 15.9 |
| L-Leucine | 39.3 | 37.9 | 36.4 | 27.6 | 32.9 |
| L-Tyrosine | 17.5 | 16.8 | 16.2 | 12.4 | 11.5 |
| L-Phenylalanine | 25.0 | 24.2 | 23.2 | 17.7 | 17.8 |
| L-Tryptophan | 9.4 | 9.7 | 9.4 | 9.8 | 8.2 |
| L-Lysine | 26.6 | 26.6 | 24.8 | 18.9 | 13.8 |
| L-Histidine | 8.1 | 8.0 | 7.4 | 5.8 | 5.8 |
| L-Arginine | 26.3 | 25.5 | 20.7 | 18.6 | 14.3 |
| Total | 424.4 | 407.5 | 387.8 | 304.8 | 299.5 |

*amino acid concentrations were determined as g A
A (amino acids)/kg biomass and are reported here as gAA/kg initial biomass taking into account dry matter losses occurring in storage. For citric acid treated algae was 1.2% and 0.4% after 24 hours and 28 days respectively. Untreated biomass experienced 4.2% and 17.8% loss after 24 hours and 28 days storage.

The change in individual amino acids varied by treatment and time. Table 7 displays the amino acid composition as grams of amino acids (gAA) per kilogram of initial biomass, taking into consideration material losses occurring in storage. Citric acid treated samples experienced less change during storage than the untreated biomass. The greatest change was observed for sulfur-containing amino acids: cysteine and methionine experienced 26% and 22% reduction after 28 days, respectively. Additionally, the amount of arginine was reduced by 21%. Threonine, serine, and GLX (glutamate and glutamine combined) were also affected by storage as evidenced by 8%, 11%, 11% reductions, respectively, after 28 days of storage. The untreated samples that experienced greater loss in storage—up to 18% loss after 28 days—likewise experienced greater changes in amino acid composition. Interestingly, the amino acids affected in untreated samples appeared to differ based on length of storage. After 24 hours aliphatic and branched chain amino acids (alanine, valine, isoleucine and leucine) were greatly reduced (28-30% reduction), whereas the concentration of these amino acids were only 9-16% reduced from the initial biomass after 28 days. Valine was the least affected, and leucine was the most affected. Other amino acids (ASX or aspartate-asparagine, threonine, serine, tyrosine, lysine and arginine) saw greater losses at longer storage times. After 28 days of storage the largest reduction (48%) was observed in lysine concentration in the untreated biomass.

Total protein losses for both 24 hour and 28 day untreated algae biomass were similar at 28% db and 29% db, respectively, in protein content.

Example 12

Changes to Amino Acid Metabolism

A total of 47 proteins associated with amino acid metabolic pathways were found to be expressed at different levels after storage compared to the initial biomass, as shown in Table 8. The changes to these metabolic pathways are believed to be due to changes in amino acid composition due to long-term storage (28 days) but not over the short term (24 hrs). Proteins associated with the metabolism of alanine, aspartate, proline and glutamate saw the largest number of proteins affected with 17 proteins that were differentially expressed. Followed by proteins involved in glycine, serine and threonine metabolism with 11. Interestingly, the untreated biomass stored for 24 hours saw no change in expression of these proteins despite this sample experiencing the greatest change in amino acid content and composition. The citric acid-treated sample also saw few changes (8 proteins) and the low number of proteins that changed in abundance in the short term (24 hrs) could indicate that changes to expression of proteins involved in amino acid metabolism take longer to occur. The extensive reduction in total amino acids of the 24 hr stored untreated algae biomass indicated that the proteins needed to affect these changes were present in sufficient quantity at the time of storage.

Some amino acids saw an increase in abundance with storage. For both treatments at each storage length, tryptophan quantities increased compared to the initial material. Proteomic analysis identified several proteins with higher expression along the pathway for tryptophan synthesis. The branched-chain amino acids valine, leucine and isoleucine were found to be increased in the untreated algae biomass after 28 days storage. The proteins that function in the initial biosynthetic reactions in each of these three pathways were also found in higher abundance after 28 days storage for both citric acid treated and untreated biomass.

TABLE 8

Changes in proteins involved in amino acid metabolism due to algae biomass treatment and storage

| Amino acid metabolic pathway | Total proteins changed | Citric acid treated (proteins changed) | | Untreated (proteins changed) | |
| --- | --- | --- | --- | --- | --- |
| | | 24 hrs | 28 days | 24 hrs | 28 days |
| Total differentially expressed proteins related to AA | 47 | 8 | 44 | 0 | 20 |
| Arginine Biosynthesis | 3 | 0 | 3 | 0 | 2 |
| Alanine, aspartate and glutamate/proline metabolism | 17 | 2 | 15 | 0 | 10 |
| Histidine metabolism | 6 | 3 | 5 | 0 | 2 |
| Glycine, serine and Threonine metabolism | 11 | 2 | 11 | 0 | 2 |
| Valine, leucine and isoleucine biosynthesis | 4 | 0 | 4 | 0 | 2 |
| Phenylalanine, tyrosine, and tryptophan biosynthesis | 6 | 1 | 6 | 0 | 2 |

While the disclosure may be susceptible to various modifications and alternative forms, specific embodiments have been shown by way of example in the Examples and drawings and have been described in detail herein. However, it should be understood that the disclosure is not intended to be limited to the particular forms disclosed. Rather, the disclosure is to cover all modifications, equivalents, and alternatives falling within the scope of the disclosure as defined by the following appended claims and their legal equivalents.

What is claimed is:

1. A method of producing succinic acid from a biomass, the method comprising:
   adding citric acid to a biomass comprising microalgae to form an acidified microalgae biomass composition;
   storing the acidified microalgae biomass composition under anaerobic conditions without inoculating the acidified microalgae biomass composition with bacteria formulated to produce succinic acid; and
   producing a coproduct comprising succinic acid in an amount between 20% on a dry weight basis of a total biomass and 50% on a dry weight basis of the total biomass.

2. The method of claim 1, wherein adding citric acid to a biomass comprises adding an aqueous citric acid solution consisting essentially of citric acid to the biomass.

3. The method of claim 1, wherein adding citric acid to a biomass comprising microalgae comprises adding a citric acid solution to the biomass comprising microalgae, and further comprising a herbaceous biomass.

4. The method of claim 1, wherein adding citric acid to a biomass comprising microalgae comprises adding the citric acid to the biomass comprising a pH of greater than about 6.0.

5. The method of claim 1, wherein adding citric acid to a biomass comprising microalgae comprises adding citric acid and one or more of lactic acid, acetic acid, or sulfuric acid to the biomass.

6. The method of claim 1, wherein adding citric acid to a biomass comprising microalgae to form an acidified microalgae biomass composition comprises forming the acidified microalgae biomass composition without adding succinic acid.

7. The method of claim 1, wherein producing a coproduct comprising succinic acid comprises producing the succinic acid at about 30% dry basis.

8. The method of claim 1, further comprising exposing the acidified microalgae biomass composition to carbon dioxide, nitrogen, or a combination thereof.

9. A method of producing succinic acid from a biomass, the method comprising:
   adding between about 1% dry weight basis and about 7% dry weight basis of citric acid to a biomass comprising microalgae to form an acidified microalgae biomass composition;
   storing the acidified microalgae biomass composition under anaerobic conditions; and
   exposing the acidified microalgae biomass composition to carbon dioxide, nitrogen, or a combination thereof to produce a coproduct comprising succinic acid in an amount between 20% on a dry weight basis of a total biomass and 50% on a dry weight basis of the total biomass.

10. The method of claim 9, wherein adding citric acid to a biomass comprising microalgae comprises adding a citric acid solution to the biomass comprising microalgae comprising at least one microalgal strain.

11. The method of claim 9, wherein adding citric acid to a biomass comprising microalgae comprises adding the citric acid to a biomass comprising *Scenedesmus* and corn stover.

12. The method of claim 9, wherein adding citric acid to a biomass comprising microalgae comprises adding the citric acid to the biomass without inoculating the biomass with bacteria.

13. The method of claim 9, wherein storing the acidified microalgae biomass composition under anaerobic conditions comprises storing the acidified microalgae biomass composition under the anaerobic conditions for at least about 30 days.

14. The method of claim 9, wherein storing the acidified microalgae biomass composition under anaerobic conditions comprises storing the acidified microalgae biomass composition in a vessel comprising a headspace.

15. The method of claim 9, wherein producing a coproduct comprising succinic acid comprises producing the succinic acid in-situ from the acidified microalgae biomass composition.

16. The method of claim 9, wherein producing a coproduct comprising succinic acid comprises producing the succinic acid while exhibiting a dry matter loss of the biomass of less than about 5% dry basis.

17. The method of claim 9, further comprising recovering the succinic acid.

18. The method of claim 17, wherein recovering the succinic acid comprises conducting one or more filtration acts on the acidified microalgae biomass composition.

19. The method of claim 18, wherein conducting one or more filtration acts on the acidified microalgae biomass composition comprises conducting one or more microfiltration act on the acidified microalgae biomass composition, one or more nanofiltration act on the acidified microalgae biomass composition, or a combination of microfiltration acts and nanofiltration acts on the acidified microalgae biomass composition.

20. The method of claim 9, wherein exposing the acidified microalgae biomass composition to carbon dioxide, nitrogen, or a combination thereof to produce a coproduct comprising succinic acid comprises preserving a protein content of the acidified microalgae biomass at from about 80% dry basis to about 95% dry basis.

* * * * *